United States Patent
Hong et al.

(10) Patent No.: US 12,005,575 B2
(45) Date of Patent: Jun. 11, 2024

(54) POWER TRANSMISSION SYSTEM FOR DRIVING ROBOT JOINT

(71) Applicants: Korea University Research and Business Foundation, Seoul (KR); ENDO ROBOTICS CO., LTD., Seoul (KR)

(72) Inventors: Daehie Hong, Seoul (KR); Byung Gon Kim, Seoul (KR); Jinwoo Choi, Seoul (KR); Chae Dong Lee, Pohang-si (KR); Jung Hyun Im, Seoul (KR); Hyuk Soon Choi, Seoul (KR); Jeonghan Kim, Anyang-si (KR)

(73) Assignees: Korea University Research and Business Foundation, Seoul (KR); ENDO ROBOTICS CO., LTD., Seoul (KR)

( * ) Notice: Subject to any disclaimer, the term of this patent is extended or adjusted under 35 U.S.C. 154(b) by 386 days.

(21) Appl. No.: 17/434,592

(22) PCT Filed: Feb. 26, 2020

(86) PCT No.: PCT/KR2020/002737
§ 371 (c)(1),
(2) Date: Aug. 27, 2021

(87) PCT Pub. No.: WO2020/175910
PCT Pub. Date: Sep. 3, 2020

(65) Prior Publication Data
US 2022/0134541 A1    May 5, 2022

(30) Foreign Application Priority Data

Feb. 27, 2019  (KR) .................. 10-2019-0023402
Feb. 14, 2020  (KR) .................. 10-2020-0018283
Feb. 14, 2020  (KR) .................. 10-2020-0018284

(51) Int. Cl.
    B25J 9/00      (2006.01)
    A61B 34/30     (2016.01)
    (Continued)

(52) U.S. Cl.
    CPC ............... B25J 9/104 (2013.01); A61B 34/30 (2016.02); B25J 9/126 (2013.01); B25J 18/06 (2013.01)

(58) Field of Classification Search
    CPC ... B25J 9/104; B25J 9/126; B25J 18/06; B25J 9/1045; A61B 34/30; A61B 2017/00477; A61B 34/71; A61B 2034/301
    See application file for complete search history.

(56) References Cited

U.S. PATENT DOCUMENTS 8,414,598 B2 *  4/2013  Brock .................... A61B 34/71
                                                        606/130
2013/0304084 A1  11/2013  Beira et al.

FOREIGN PATENT DOCUMENTS

CN    105407781 A    3/2016
CN    107735041 A    2/2018
(Continued)

OTHER PUBLICATIONS

English Translation of KR20140001572 (Year: 2014).*
(Continued)

*Primary Examiner* — Victor L MacArthur
(74) *Attorney, Agent, or Firm* — Sughrue Mion, PLLC

(57) ABSTRACT

A power transmission system for driving a robot joint includes a driving part including a first driving unit and a second driving unit, a first force transmission part including a first sheath formed to have a predetermined length, flexibility, and a hollow shape and a first wire which is inserted into the first sheath and of which one end is fixed to a joint of a robot and the other end is connected to the first driving (Continued)

unit, and a second force transmission part including a second sheath formed to have a predetermined length, flexibility, and a hollow shape and a second wire which is inserted into the second sheath and of which one end is fixed to the joint of the robot and the other end is connected to the second driving unit.

20 Claims, 20 Drawing Sheets

(51) Int. Cl.
    *B25J 9/10*     (2006.01)
    *B25J 9/12*     (2006.01)
    *B25J 18/06*     (2006.01)

(56) References Cited

FOREIGN PATENT DOCUMENTS

| | | |
|---|---|---|
| EP | 3025630 A1 | 6/2016 |
| JP | 4-218135 A | 8/1992 |
| JP | 2008-514381 A | 5/2008 |
| JP | 2008-284156 A | 11/2008 |
| JP | 2014-504897 A | 2/2014 |
| JP | 2015-159844 A | 9/2015 |
| KR | 10-2011-0069114 A | 6/2011 |
| KR | 10-2014-0001572 A | 1/2014 |
| KR | 10-1889065 B1 | 8/2018 |
| KR | 2020-0104710 A | 9/2020 |
| WO | 2017205310 A1 | 11/2017 |
| WO | 2019006087 A2 | 1/2019 |
| WO | 2019006087 A3 | 1/2019 |

OTHER PUBLICATIONS

International Search Report for PCT/KR2020/002737 dated Jun. 11, 2020 [PCT/ISA/210].
Written Opinion for PCT/KR2020/002737 dated Jun. 11, 2020 [PCT/ISA/237].
Chinese Office Action dated Jan. 25, 2024 in Application No. 202080017325.4.

* cited by examiner

POWER TRANSMISSION SYSTEM FOR DRIVING ROBOT JOINT

CROSS REFERENCE TO RELATED APPLICATIONS

This application is a National Stage of International Application No. PCT/KR2020/002737 filed Feb. 26, 2020, claiming priority based on Korean Patent Application No. 10-2019-0023402 filed Feb. 27, 2019, Korean Patent Application No. 10-2020-0018283 filed Feb. 14, 2020 and Korean Patent Application No. 10-2020-0018284 filed Feb. 14, 2020.

TECHNICAL FIELD

The present invention relates to a surgical robot, and more specifically, to a power transmission system for driving a robot joint.

BACKGROUND ART

Recently, as an application range of robots has been expanded in various fields such as industry and medical fields, various actuation methods are being developed. Power is transmitted using various methods using belts, chains, or wires in addition to directly attaching an actuator to a robot joint.

Among actuation methods, the simplest method is to directly attach an actuator to a link structure, but there is a disadvantage in that the actuator is very heavy.

To compensate for this, a double-input cable driving method in which an actuator is fixed to a floor and transmits a force using two flexible cables was proposed.

However, in the conventional cable driving method, since the two cables are driven only in a case in which both of two motors pull the cables, one motor should provide a force capable of pulling both of the two cables, that is, a master cable and a slave cable, in order to transmit a driving force to a target object.

Accordingly, when the two cables are driven, since each of the motors should pull the master cable using a very large force, a motor having high output power is required, and thus there is a problem of low precision.

In addition, in the case of the conventional driving method, since the motor applies the force, which directly pulls the master cable, to the master cable, there is no big problem with the master cable, but in the slave cable which is driven by a force applied by the master cable, since a portion, which is not inserted into a sheath and is exposed to the outside, of the slave cable is loosened to be bent or to generate large back lash, there is a problem of low precision.

Accordingly, a method of reducing back lash is required without loosening and bending a slave cable.

In addition, since such a cable is inserted through a body part, a disposable cable, which is not reused, is used as the cable in order to prevent a patient from being infected. After the cable is used, the cable is separated from a driving apparatus and replaced with a new cable, and thus, there is an inconvenience of coupling the cable to the driving apparatus again.

DISCLOSURE

Technical Problem

The present invention is directed to providing a power transmission system for driving a robot joint capable of controlling movement of a slave cable to increase a power transmission amount and improve control precision.

In addition, the present invention is directed to providing a cartridge type power transmission system for driving a robot joint which allows a disposable cable to be conveniently replaced.

Objectives of the present invention are not limited to the objectives described above, and the other objectives, which are not described above, will be clearly understood by those skilled in the art from the following descriptions.

Technical Solution

One aspect of the present invention provides a power transmission system for driving a robot joint, which is a system for driving a joint of a robot, the power transmission system including a driving part including a first driving unit and a second driving unit, a first force transmission part including a first sheath formed to have a predetermined length, flexibility, and a hollow shape and a first wire which is inserted into the first sheath and of which one end is fixed to a joint of a robot and the other end is connected to the first driving unit, and a second force transmission part including a second sheath formed to have a predetermined length, flexibility, and a hollow shape and a second wire which is inserted into the second sheath and of which one end is fixed to the joint of the robot and the other end is connected to the second driving unit, wherein, in a case in which the first driving unit provides a force to the first wire in a first direction, the second driving unit provides a force to the second wire in a second direction opposite to the first direction.

In a case in which the first driving unit applies a force to the first wire in a direction in which the first wire is pulled, the second driving unit may provide a force to the second wire in a direction in which the second wire is pushed, and in a case in which the second driving unit applies a force to the second wire in a direction in which the second wire is pulled, the first driving unit may provide a force to the first wire in a direction in which the first wire is pushed.

In a case in which the first driving unit provides a force to the first wire in a direction in which the first wire is pulled, and the second driving unit provides a force to the second wire in a direction in which the second wire is pushed, a magnitude of the force provided to the second wire by the second driving unit may be adjusted according to a friction force generated between the second wire and the second sheath.

A magnitude of a maximum force provided to the second wire by the second driving unit may be the same as a magnitude of the friction force generated between the second wire and the second sheath.

In a case in which the first driving unit provides a force to the first wire in a direction in which the first wire is pulled and the second driving unit provides a force to the second wire in a direction in which the second wire is pushed, a magnitude of the force provided to the first wire by the first driving unit may be the same as a sum of a magnitude of a friction force generated between the first wire and the first sheath and a magnitude of a force which moves the joint of the robot In a case in which the first driving unit provides a force to the first wire in a direction in which the first wire is pulled and the second driving unit provides a force to the second wire in a direction in which the second wire is pushed, a withdrawal length of the first wire withdrawn from an outer side of an end portion of the first sheath may be relatively greater than an insertion length of the second wire inserted into the second sheath from an end portion of the second sheath.

In the case in which the first driving unit provides the force to the first wire in the direction in which the first wire is pulled and the second driving unit provides the force to the second wire in the direction in which the second wire is pushed, a partial length, which includes the end portion of the second sheath into which the second wire is inserted, of an entire length of the second sheath may be in a state in which movement of the partial length is prevented with the second wire.

In addition, in a case in which the first driving unit, to which the other end portion of the first wire having one end fixed to the robot joint and inserted into the first sheath is connected and which provides a force that pulls or pushes the first wire in a longitudinal direction of the first sheath, and the second driving unit, to which the other end portion of the second wire having one end fixed to the robot joint and inserted into the second sheath is connected and which provides a force that pulls or pushes the second wire in a longitudinal direction of the second sheath are included, when the first driving unit provides a force to the first wire in the first direction, a power transmission method of driving a robot joint may be provided as a cable power transmission method of driving a joint of a robot, wherein the method may include providing a force to the second wire using the second driving unit in the second direction opposite to the first direction.

The power transmission system for driving a robot joint may further include a body part, a first elastic part of which one end is fixed to the body part and the other end is fixed to the first driving unit and which wraps the other end of the first wire, and a second elastic part of which one end is fixed to the body part and the other end is fixed to the second driving unit and which wraps the other end of the second wire, wherein the first driving unit and the second driving unit may move linearly.

The power transmission system for driving a robot joint may further include a control part disposed in the body part, wherein the control part may control the first driving unit to provide the force to the first wire in the first direction and control the second driving unit to provide the force to the second wire in the second direction opposite to the first direction.

A first wire hole through which the first wire passes and a second wire hole through which the second wire passes may be formed in one side of the body part.

The first driving unit may include a first driving motor which generates a driving force and a first moving part which receives the driving force of the first driving motor to move linearly, and the second driving unit may include a second driving motor which generates a driving force and a second moving part which receives the driving force of the second driving motor to move linearly.

The body part may include a first guide hole which guides the first moving part, and a second guide hole which guides the second moving part.

Each of the first elastic part and the second elastic part receives a force in the first direction to contract and receives a force in the second direction to extend.

In addition, another aspect of the present invention provides a cartridge type power transmission system for driving a robot joint, which is a power transmission system for driving a joint of a robot, the cartridge type power transmission system including a housing, a first driving part disposed in the housing and moved linearly, and a cartridge inserted into the housing, wherein the cartridge includes a case, a moving part accommodated in the case, connected to the first driving part, and moved linearly, a force transmission part including a sheath formed to have a predetermined length, flexibility, and a hollow shape and a wire which is inserted into the sheath, of which one end is fixed to a joint of a robot and the other end is fixed to the moving part, and which passes through the case, and an elastic part of which one end is fixed to the case and the other end is fixed to the moving part and which wraps the wire, and the cartridge is detachably coupled to the housing.

The cartridge type power transmission system may further include a second driving part which moves the first driving part so that the first driving part is connected to or separated from the moving part.

The first driving part may include a driving body part which is movable in the housing, a first motor disposed in the driving body part, and a detachable part connected to the first motor, moved linearly by a driving force of the first motor, and detachably coupled to the moving part.

The second driving part may include a second motor disposed in the housing, and a connection part connected to the second motor and moved linearly by a driving force of the second motor.

The detachable part may include a protrusion protruding from an outer surface of the detachable part, and the moving part may include a detachable groove into which the protrusion of the detachable part is inserted.

The cartridge may include a hole through which the force transmission part passes.

The case may include a guide hole which guides movement of the moving part.

The elastic part may extend in a first direction and contract in a second direction opposite to the first direction.

Advantageous Effects

According to an embodiment of the present invention, since a driving unit provides a driving force to a slave cable to cancel a friction force generated by the slave cable, even when a driving force having a small magnitude is provided to a master cable, a power transmission amount at a level which is greater than or equal to that in a conventional case can be obtained.

In addition, according to the embodiment of the present invention, since a friction force generated by the slave cable is canceled to prevent or reduce back lash at the slave cable, there is an advantage of improving control precision.

In addition, since a cartridge including the cable is detachably coupled to a housing, the cable used in surgery can be easily replaced.

In addition, since the cable is driven by the cartridge being inserted into the housing, hygiene management of a surgical robot driving apparatus is improved when compared to a conventional case in which there is an infection risk in a process of connecting a cable to a driving apparatus.

REFERENCE NUMERALS

Figure 1:
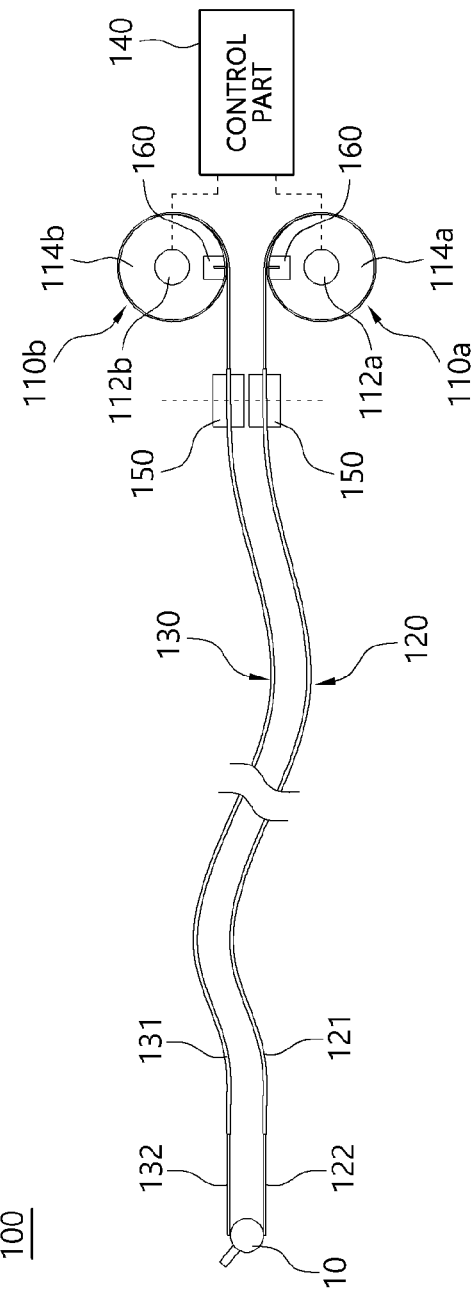
FIG. 1 is a schematic view illustrating a power transmission system for driving a robot joint according to one embodiment of the present invention.

100: POWER TRANSMISSION SYSTEM FOR DRIVING ROBOT JOINT
110A: FIRST DRIVING UNIT
112A: FIRST DRIVING MOTOR
114A: FIRST ROLLER
110B: SECOND DRIVING UNIT
112B: SECOND DRIVING MOTOR
114B: SECOND ROLLER
120: FIRST FORCE TRANSMISSION PART
121: FIRST SHEATH
122: FIRST WIRE
130: SECOND FORCE TRANSMISSION PART
131: SECOND SHEATH
132: SECOND WIRE
140: CONTROL PART
150: SHEATH HOLDER
160: WIRE HOLDER
200, 200A, 200B: CABLE DRIVING APPARATUS FOR DRIVING ROBOT JOINT
210: MAIN BODY
212: ARRANGEMENT HOLE
220: DRIVING MOTOR
230: DRIVING ROLLER
232: FIRST ACCOMMODATION GROOVE
234: SEATING GROOVE
240: WEIGHT MEASUREMENT PART
242: SECOND ACCOMMODATION GROOVE
250: COVER
251: COVER SURFACE
252: GUIDE GROOVE
252A: FIRST GUIDE GROOVE
252B: SECOND GUIDE GROOVE
300: POWER TRANSMISSION SYSTEM FOR DRIVING ROBOT JOINT
310: BODY PART
361: FIRST DRIVING UNIT
371: SECOND DRIVING UNIT
320: FIRST FORCE TRANSMISSION PART
321: FIRST SHEATH
322: FIRST WIRE
330: SECOND FORCE TRANSMISSION PART
331: SECOND SHEATH
332: SECOND WIRE
340: FIRST ELASTIC PART
350: SECOND ELASTIC PART
400: CARTRIDGE TYPE POWER TRANSMISSION SYSTEM FOR DRIVING ROBOT JOINT
410: HOUSING
420: FIRST DRIVING PART
430: CARTRIDGE

MODES OF THE INVENTION

Hereinafter, various embodiments will be described in detail with reference to the accompanying drawings. The embodiments according to the present invention may be variously changed. Specific embodiments may be illustrated in the drawings and described in detail in the modes of the invention. However, the accompanying specific embodiments are only for various embodiments to be easily understood. Accordingly, the technical spirit is not limited to the specific embodiments illustrated in the accompanying drawings and should be understood to cover all modifications, equivalents, and alternatives falling within the spirit and scope of the invention.

Although the terms "first," "second," and the like may be used herein to describe various elements, these elements should not be limited by these terms. These terms are only used for distinguishing one element from another.

It should be understood that the terms "comprises," "comprising," "includes," and/or "including," in the embodiment of the present invention, specify the presence of stated features, integers, steps, operations, elements, components, and/or groups thereof but do not preclude the presence or addition of one or more other features, integers, steps, operations, elements, components, and/or groups thereof. In the present specification, when an element is referred to as being "connected" or "coupled" to another element, it will be understood that the element can be directly connected or coupled to another element, or intervening elements may be present therebetween. In contrast, when an element is referred to as being "directly connected" or "directly coupled" to another element, it will be understood there are no intervening elements.

Meanwhile, a "module" or "part" among components used in the embodiment performs at least one function or operation. In addition, the "module" or "part" may perform the function or operation using hardware, software, or combination thereof. In addition, a plurality of "modules" or "parts" excluding a "module" or "part" which should be performed by specific hardware or at least one processor may also be integrated as at least one module. The description of a singular form in the present specification includes a description of a plural form unless the context clearly indicates otherwise.

In addition, when the embodiments of the present invention are described, in a case in which it is determined that the detailed descriptions may unnecessarily obscure the gist of the present invention, the detailed descriptions of known functions and configurations related to the present invention will be reduced or omitted.

Figure 2:
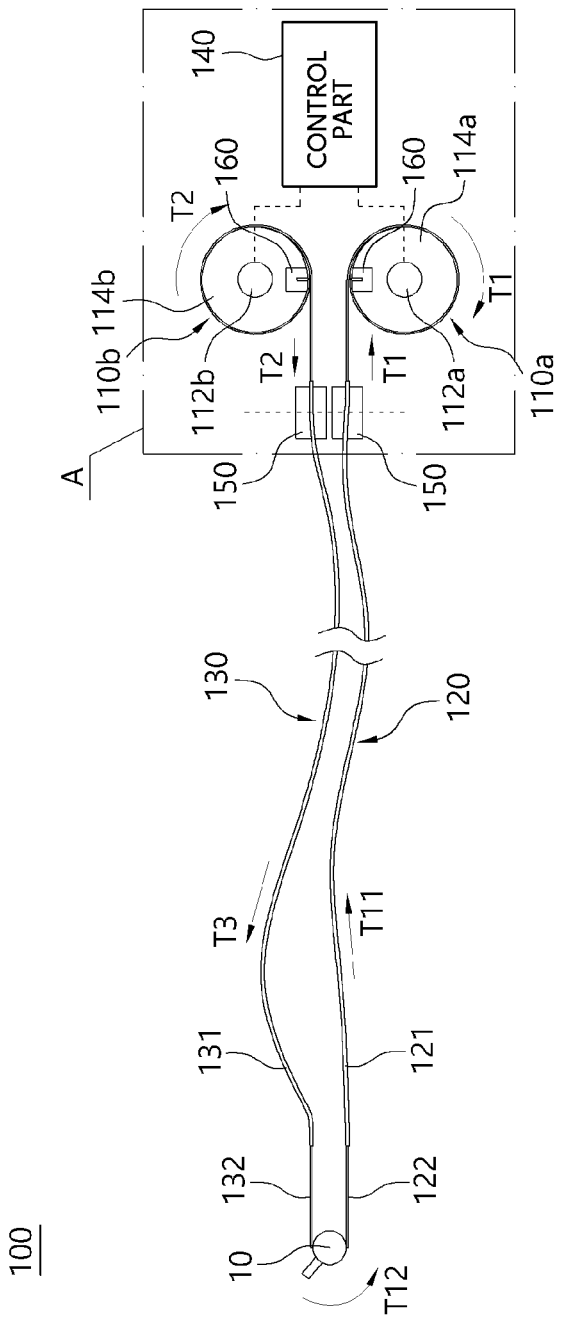
FIG. 2 is a view illustrating an operation state of that of FIG. 1.

A power transmission system 100 for driving a robot joint according to one embodiment of the present invention realizes a double input sheath-tendon power transmission mechanism and includes a driving part, a first force transmission part 120, and a second force transmission part 130 as illustrated in FIGS. 1 and 2.

That is, in the power transmission system 100 for driving a robot joint according to one embodiment of the present invention, the driving part may include a first driving unit 110a and a second driving unit 110b, the first driving unit 110a may be directly connected to the first force transmission part 120 and may provide a driving force to the first force transmission part 120, and the second driving unit 110b may be directly connected to the second force transmission part 130 and may provide a driving force to the second force transmission part 130.

In the present invention, in each of the first force transmission part 120 and the second force transmission part 130, a sheath-tendon mechanism in which a tendon is inserted into a sheath to be moved in a longitudinal direction therein may be employed.

That is, the first force transmission part 120 may include a first sheath 121 having a predetermined length, flexibility, and a hollow shape and a first wire 122 inserted into the first sheath 121. In this case, the first wire 122 may be inserted into the first sheath 121 so that both end portions of the first wire 122 are exposed to the outside of the first sheath 121, one end portion of both of the end portions, which are exposed to the outside, of the first wire 122 may be fixed to a control target object 10, and the other end portion thereof may be fixed to the first driving unit 110a.

Similarly, the second force transmission part 130 may include a second sheath 131 having a predetermined length, flexibility, and a hollow shape and a second wire 132 inserted into the second sheath 131. In this case, the second wire 132 may be inserted into the second sheath 131 so that both end portions of the second wire 132 are exposed to the outside of the second sheath 131, and one end portion of both of the end portions, which are exposed to the outside, of the second wire 132 may be fixed to the control target object 10, and the other end portion thereof may be fixed to the second driving unit 110b.

In addition, the first driving unit 110a may include a first driving motor 112a and a first roller 114a rotatably coupled to the first driving motor 112a, and one end portion of the first wire 122 may be fixedly coupled to the first roller 114a.

Similarly, the second driving unit 110b may include a second driving motor 112b and a second roller 114b rotatably coupled to the second driving motor 112b, and one end portion of the second wire 132 may be fixedly coupled to the second roller 114b.

In the present invention, the control target object 10 may be a driving joint of a robot, and the driving joint of the robot may be a driving joint for driving a finger or a wrist of the robot in a robot arm. In addition, each of the first sheath 121 and the second sheath 131 may be a coil shaped tube formed of a metal material to withstand tension applied to each of the first wire 122 and the second wire 132, to maintain an overall shape, and to have flexibility. However, the shape and the material of each of the first sheath 121 and the second sheath 131 are not limited thereto, and any shape and any material employed for a sheath in a known sheath-tendon mechanism may be applied thereto.

In addition, the power transmission system 100 for driving a robot joint according to one embodiment of the present invention may further include a control part 140 for controlling overall operations of the first driving unit 110a and the second driving unit 110b, and the control part 140 may control driving of the first driving unit 110a and driving of the second driving unit 110b on the basis of an input signal of a user. In addition, the control part 140 may control a magnitude of a force provided to the first wire 122 from the first driving unit 110a and a magnitude of a force provided to the second wire 132 from the second driving unit 110b on the basis of the input signal of the user.

As described above, in the power transmission system 100 for driving a robot joint according to one embodiment of the present invention, the first force transmission part 120 in which the end portion of the first wire 122 is connected to the first driving unit 110a and the second force transmission part 130 in which the end portion of the second wire 132 is connected to the second driving unit 110b may be connected by the control target object 10, and in a case in which a driving force is transmitted to the first wire 122 from the first driving unit 110a, or a driving force is transmitted to the second wire 132 from the second driving unit 110b through control of the control part 140, the first wire 122 and the second wire 132 may move in the longitudinal directions in the first sheath 121 and the second sheath 131, respectively. Accordingly, the control target object 10 may be rotated or moved to a position desired by the user.

In this case, in the power transmission system 100 for driving a robot joint according to one embodiment of the present invention, unlike a conventional double input sheath-tendon mechanism, the first driving unit 110a and the second driving unit 110b may provide a driving force to the first force transmission part 120 and a driving force to the second force transmission part 130 at the same time, and a magnitude of the driving force provided to the first force transmission part 120 and a magnitude of the driving force provided to the second force transmission part 130 from the first driving unit 110a and the second driving unit 110b, respectively, may be controlled by the control part 140.

Figure 3:
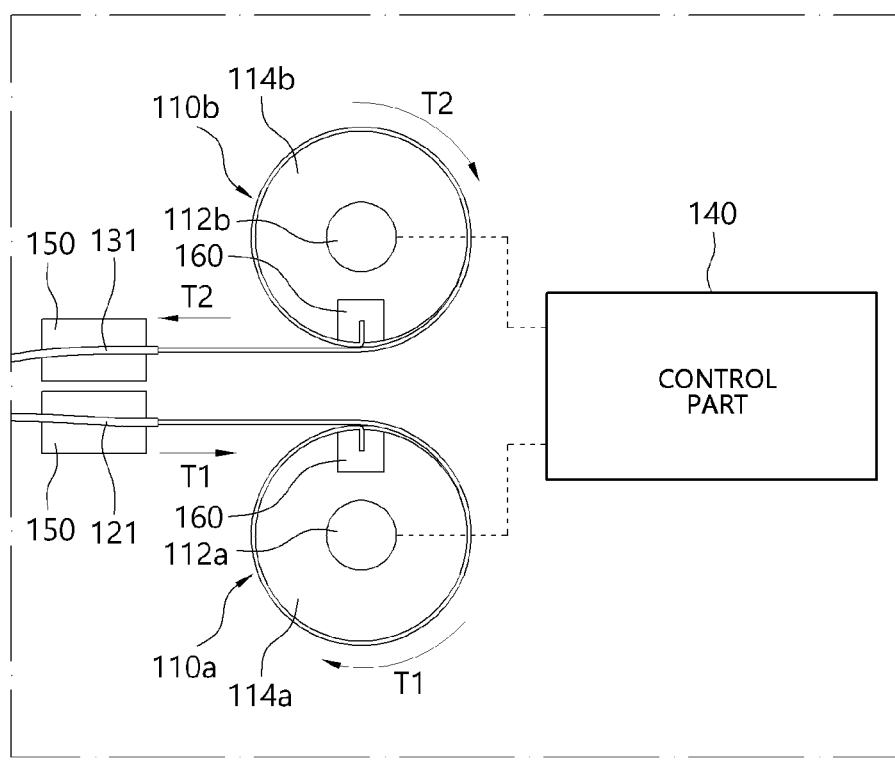
FIG. 3 is an enlarged view illustrating a portion A in FIG. 2.

That is, as illustrated in FIGS. 2 and 3, in the power transmission system 100 for driving a robot joint according to one embodiment of the present invention, in a case in which the first driving unit 110a provides a force to the first wire 122 in a first direction, the second driving unit 110b may provide a force to the second wire 132 in a second direction opposite to the first direction.

Similarly, in the power transmission system 100 for driving a robot joint according to one embodiment of the present invention, in a case in which the second driving unit 110b provides a force to the second wire 132 in the first direction, the first driving unit 110a may provide a force to the first wire 122 in the second direction opposite to the first direction.

In the present invention, the first direction is defined as a direction of a force by which the first driving unit 110a pulls the first wire 122 or a direction of a force by which the second driving unit 110b pulls second wire 132, and the second direction is defined as a direction of a force by which the first driving unit 110a pushes the first wire 122, or a direction of a force by which the second driving unit 110b pushes the second wire 132.

In addition, in the first wire 122 and the second wire 132, a role of a master cable and a role of a slave cable may be interchanged according to directions of forces provided from the first driving unit 110a and the second driving unit 110b.

That is, in a case in which the first wire 122 moves in the first direction and the second wire 132 moves in the second direction, the first wire 122 may serve as the master cable, and the second wire 132 may serve as the slave cable. Conversely, in a case in which the first wire 122 moves in the second direction and the second wire 132 moves in the first direction, the second wire 132 may serve as the master cable, and the first wire 122 may serve as the slave cable.

Specifically, in a case in which the first driving unit 110a provides a force T1 to the first wire 122 in the first direction, the second driving unit 110b may provide a force T2 to the second wire 132 in the second direction. Accordingly, the control target object 10 connected to the end portion of the first wire 122 and the end portion of the second wire 132 may be rotated in the first direction as illustrated in FIG. 2.

Conversely, in a case in which the second driving unit 110b provides a force to the second wire 132 in the first direction, the first driving unit 110a may provide a force to the first wire 122 in the second direction. Accordingly, the control target object 10 connected to the end portion of the first wire 122 and the end portion of the second wire 132 may be rotated in the second direction.

That is, in the power transmission system 100 for driving a robot joint according to one embodiment of the present invention, in a case in which, among the first wire 122 and second wire 132, the force T1 is provided to any one wire serving as the master cable in the first direction in which the wire is pulled, the force T2 may be provided to the remaining wire serving as the slave cable in the second direction in which the wire is pushed.

In other words, in the power transmission system 100 for driving a robot joint according to one embodiment of the present invention, by providing the force T1 which pulls the wire serving as the master cable using the driving unit and providing the force T2 which actively pushes the wire serving as the slave cable using the driving unit at the same time, a friction force T3 generated due to contact between the wires and the sheaths in a process in which the wires moved in the sheaths may be compensated for.

Accordingly, in the power transmission system 100 for driving a robot joint according to one embodiment of the present invention, even when the wire serving as the master cable is pulled using a small force, the control target object 10 may be moved to a desired position.

Hereinafter, for the sake of convenience in the description, an example, in which the first wire 122 serves as the master cable which controls movement of the control target object 10 and the second wire 132 serves as the slave cable role, will be described, and since an opposite case, in which the second wire 132 serves as the master cable which controls movement of the control target object 10 and the first wire 122 serves as the slave cable, is the same as the example except that a magnitude and a direction of a force provided to the first wire 122 and a magnitude and a direction of a force provided to the second wire 132 are interchanged, the detailed description thereof will be omitted.

Specifically, as illustrated in FIGS. 2 and 3, in a case in which the first driving unit 110a provides the force T1 to the first wire 122 in the first direction, the second driving unit 110b may provide the force T2 to the second wire 132 in the second direction.

In this case, a magnitude of the force T2 provided to the second wire 132 in the second direction by the second driving unit 110b may be set on the basis of the friction force T3 generated between the second wire 132 and the second sheath 131 in a process in which the second wire 132 is moved toward the control target object 10 in the longitudinal direction of the second sheath 131.

Preferably, the magnitude of the force T2 provided to the second wire 132 in the second direction by the second driving unit 110b may be provided to be the same as a magnitude of the friction force T3 generated between the second wire 132 and the second sheath 131 in the process in which the second wire 132 is moved to the control target object 10 in the longitudinal direction of the second sheath 131.

Accordingly, when a magnitude of the force T1 provided to the first wire 122 in the first direction by the first driving unit 110a is the same as the sum of a magnitude of a friction force T11 generated between the first wire 122 and the first sheath 121 and a magnitude of a force T12 for moving the control target object 10 in a process in which the first wire 122 is moved toward the first driving unit 110a in the longitudinal direction of the first sheath 121, the control target object 10 may be moved to a position desired by a worker.

In this case, a magnitude of the maximum force T2 provided to the second wire 132 in the second direction by the second driving unit 110b may be the same as the magnitude of the friction force T3 generated between the second wire 132 and the second sheath 131 in the process in which the second wire 132 is moved to the control target object 10 in the longitudinal direction of the second sheath 131. In addition, the magnitude of the maximum force T2 provided to the second wire 132 in the second direction by the second driving unit 110b may be smaller than the magnitude of the force T1 provided to the first wire 122 in the first direction by the first driving unit 110a.

Figure 4:
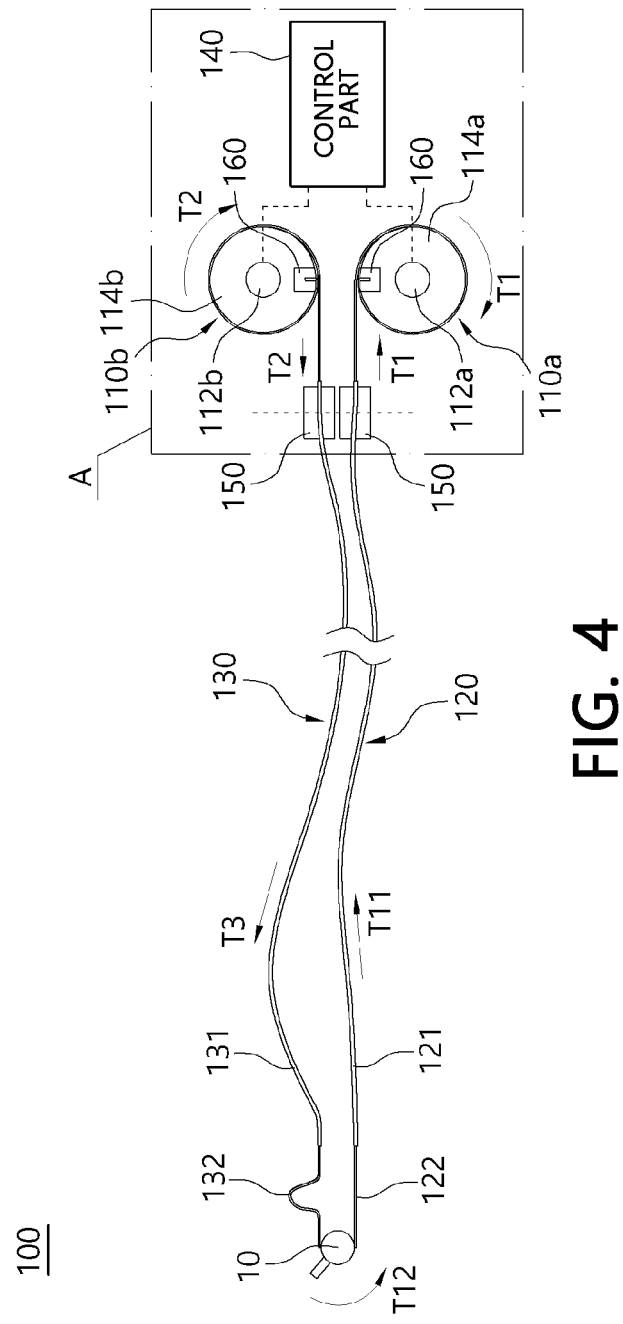
FIG. 4 is a view illustrating an operation state of a case in which a driving unit excessively provides a pushing force to a wire in FIG. 1.

This is because, as illustrated in FIG. 4, when the magnitude of the maximum force T2 provided to the second wire 132 in the second direction by the second driving unit 110b is greater than the magnitude of the friction force T3 generated between the second wire 132 and the second sheath 131, a portion, which is connected to the control target object 10 and exposed at an end portion of the second sheath 131, of the second wire 132 may be bent, and in a case in which the force T1 which pulls the first wire 122 is removed, back lash may occur at the second wire 132.

Meanwhile, in the power transmission system 100 for driving a robot joint according to one embodiment of the present invention, in a case in which a force is provided to the wire serving as the slave cable, in order for the wire to not be loosened and to be smoothly move in the sheath, the end portion of the sheath may be fixed to the driving unit 110*a* or 110*b*.

As an example, in a case in which the first driving unit 110*a* provides a force to the first wire 122 in the first direction, and the second driving unit 110*b* provides a force to the second wire 132 in the second direction at the same time, a partial length B, which includes the end portion into which the second wire 132 is inserted, of an entire length of the second sheath 131 may be in a state in which movement of the partial length B is prevented with the second wire 132.

Figure 8:
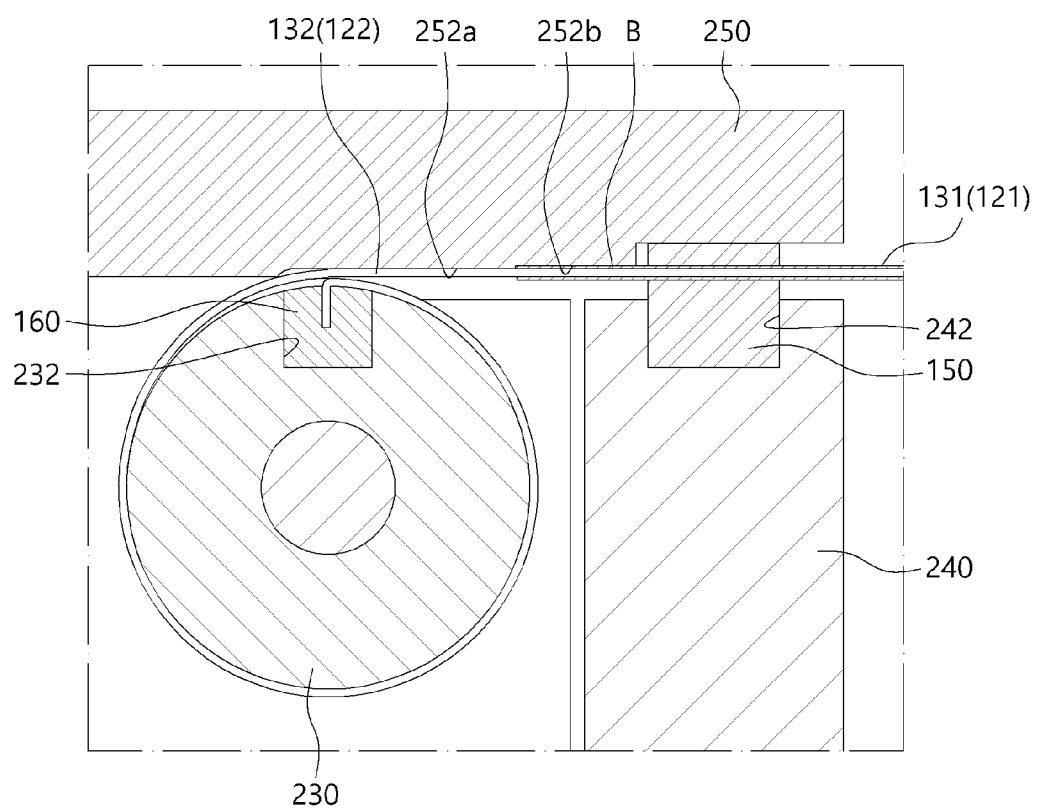
FIG. 8 is a partial cross-sectional view illustrating a state in which a wire is wound around a roller in FIG. 6.

As a non-restrictive example, the second sheath 131 may be fixed in a stated in which the partial length B, which includes the end portion into which the second wire 132 is inserted, of the entire length of the second sheath 131 is inserted into a guide groove 252 formed in a side of the second driving unit 110*b* in a direction parallel to the longitudinal direction, and the guide groove 252 may be formed so that a part, which is exposed to the outside, of the second wire 132 is seated on the guide groove 252 with the partial length B of the second sheath 131 (see FIG. 8).

Accordingly, in a case in which the second driving unit 110*b* provides a force to the second wire 132 in the second direction, since the partial length, which is exposed to the outside from the end portion of the second sheath 131, of the second wire 132 may be directly moved to the second sheath 131 along the guide groove 252, the second wire 132 can be prevented from being loosened at a side of the end portion of the second sheath 131.

As described above, in the power transmission system 100 for driving a robot joint according to one embodiment of the present invention, since the driving unit provides a driving force, which actively pushes the wire serving as the slave cable, to the wire to cancel a friction force generated between the wire serving as the slave cable and the sheath, even when a small magnitude of a driving force is provided to the wire serving as the master cable, a power transmission amount at a level which is greater than or equal to that in a conventional case can be obtained.

In addition, according to the present invention, since a friction force generated by the slave cable is canceled to prevent or reduce back lash at the slave cable, there is an advantage of improving control precision.

Meanwhile, in the power transmission system 100 for driving a robot joint according to one embodiment of the present invention, each of the first driving unit 110*a* and the second driving unit 110*b* may be implemented as a cable driving apparatus 200 for driving a robot joint.

Figure 5:
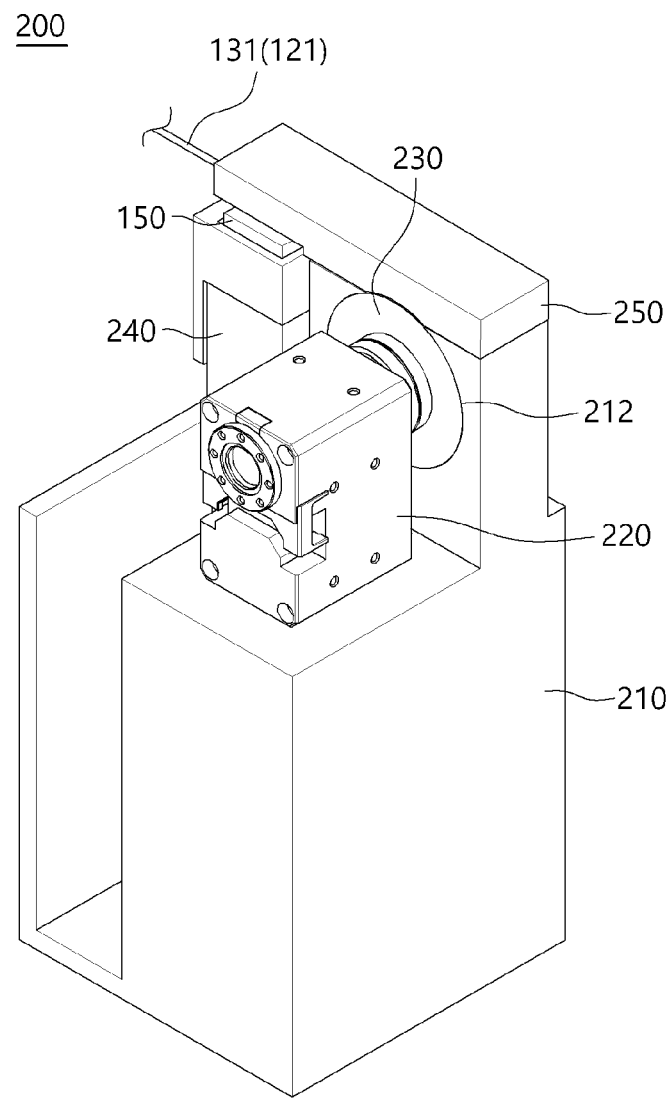
FIG. 5 is a view illustrating a cable driving apparatus for driving a robot joint which may be employed as a driving unit in the power transmission system for driving a robot joint according to one embodiment of the present invention.
Figure 6:
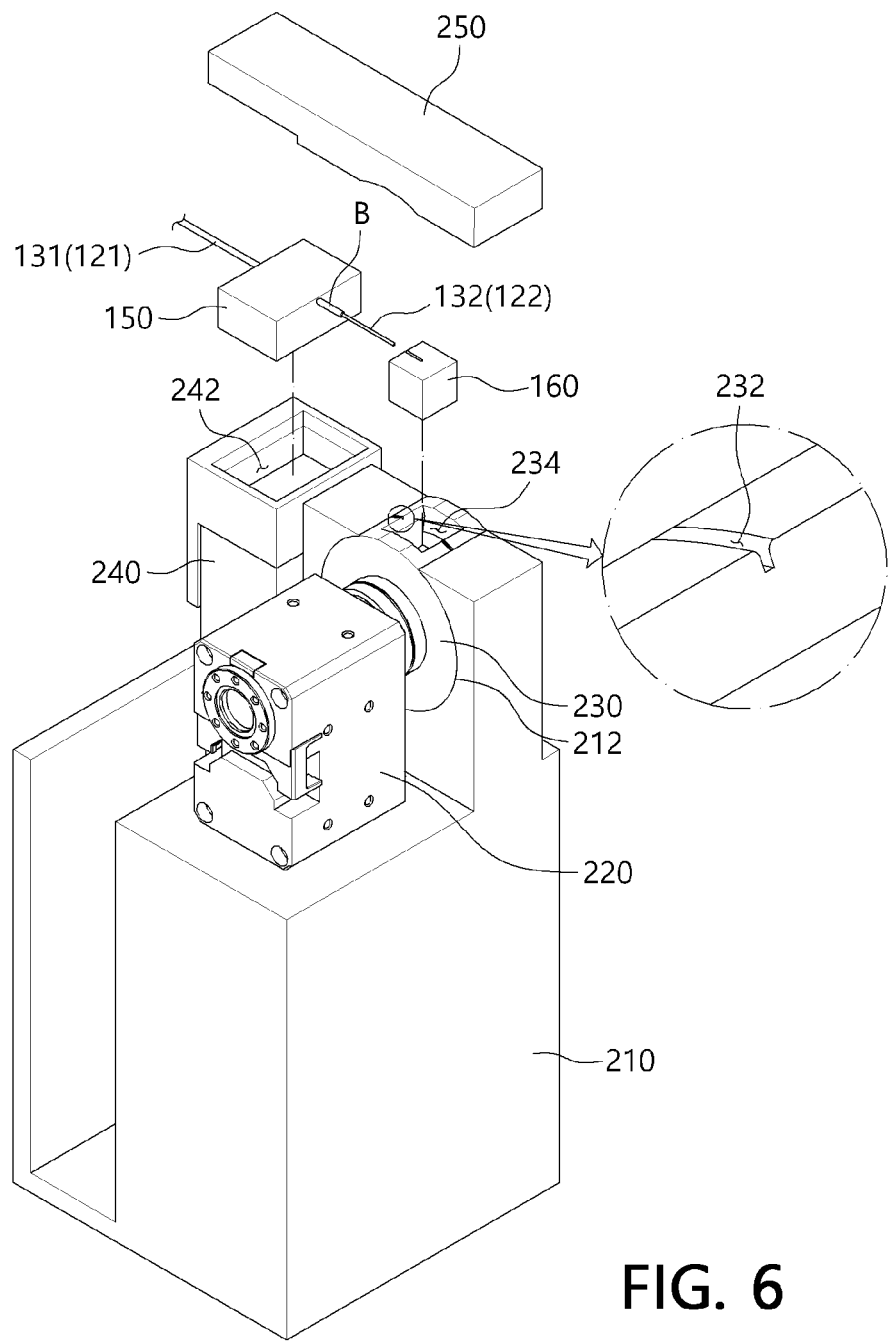
FIG. 6 is an exploded view illustrating main components in FIG. 5.
Figure 7:
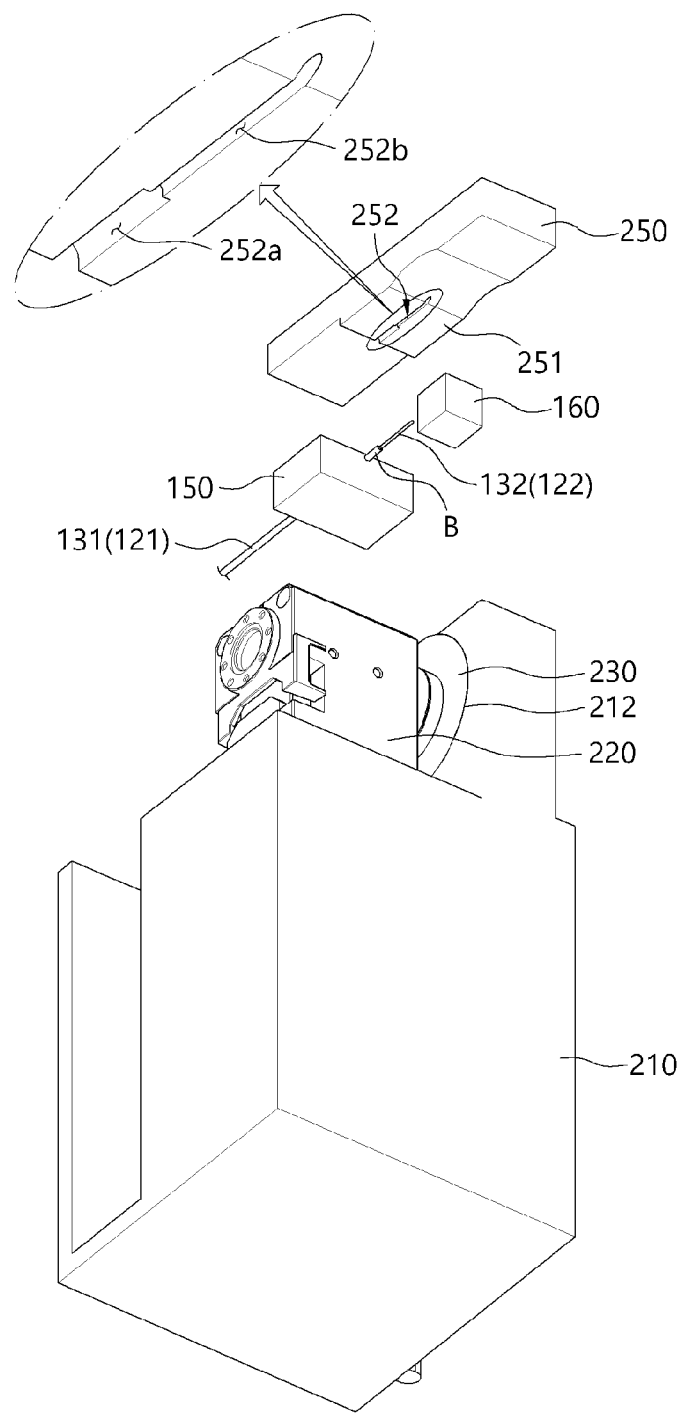
FIG. 7 is a view illustrating FIG. 6 when viewed from another side.

As an example, each of the first driving unit 110*a* and the second driving unit 110*b* may be the cable driving apparatus 200 for driving a robot joint illustrated in FIGS. 5 to 7, and in the cable driving apparatus 200 for driving a robot joint, a force that pulls a wire 122 or 132 to the outside of a sheath 121 or 131 or pushes the wire 122 or 132 into the sheath 121 or 131 may be provided by rotating a driving roller 230 using a driving motor 220 in a state in which a sheath holder 150, to which the sheath 121 or 131 is fixedly coupled, and a wire holder 160, to which an end portion of the wire 122 or 132 is fixed, are fixed.

In the present embodiment, the sheath 121 or 131 may be the first sheath 121 or the second sheath 131 described above, and the wire 122 or 132 may be the first wire 122 or the second wire 132 described above.

In addition, in the power transmission system 100 for driving a robot joint, the first driving motor 112*a* and the first roller 114*a* constituting the first driving unit 110*a* may be the driving motor 220 and the driving roller 230, respectively, which will be described below. In addition, in the power transmission system 100 for driving a robot joint, the second driving motor 112*b* and the second roller 114*b* constituting the second driving unit 110*b* may also be the driving motor 220 and the driving roller 230, respectively, which will be described below.

In this case, the sheath 121 or 131 may be fixed to the sheath holder 150 so that both end portions of the sheath 121 or 131 protrude from the sheath holder 150 by a predetermined length, the wire 122 or 132 may pass through the sheath 121 or 131 fixed to the sheath holder 150 in a state in which one end portion of the wire 122 or 132 is fixed to a control target object 10, and the other end portion thereof may be fixed to the wire holder 160.

In this state, the sheath holder 150 and the wire holder 160 may be installed in the cable driving apparatus 200 for driving a robot joint.

To this end, the cable driving apparatus 200 for driving a robot joint according to the embodiment of the present invention may include a main body 210, the driving motor 220, the driving roller 230, and a weight measurement part 240.

Specifically, the main body 210 may serve as a fixture on which the driving motor 220, the driving roller 230, and the weight measurement part 240 are installed.

As an example, the driving motor 220 may be disposed on one surface of the main body 210, and an arrangement hole 212 having a shape corresponding to the driving roller 230 may be formed in one surface of the main body 210 so that the driving roller 230 may be disposed in the arrangement hole 212.

In addition, the driving roller 230 may be driven by a driving force provided from the driving motor 220 and rotatably disposed in the arrangement hole 212, and a first accommodation groove 232 for accommodating the wire holder 160 may be formed in one side of the driving roller 230.

In this case, the driving motor 220 may include a speed reduction device, and the driving roller 230 may be rotatably coupled to the speed reduction device.

Figure 9:
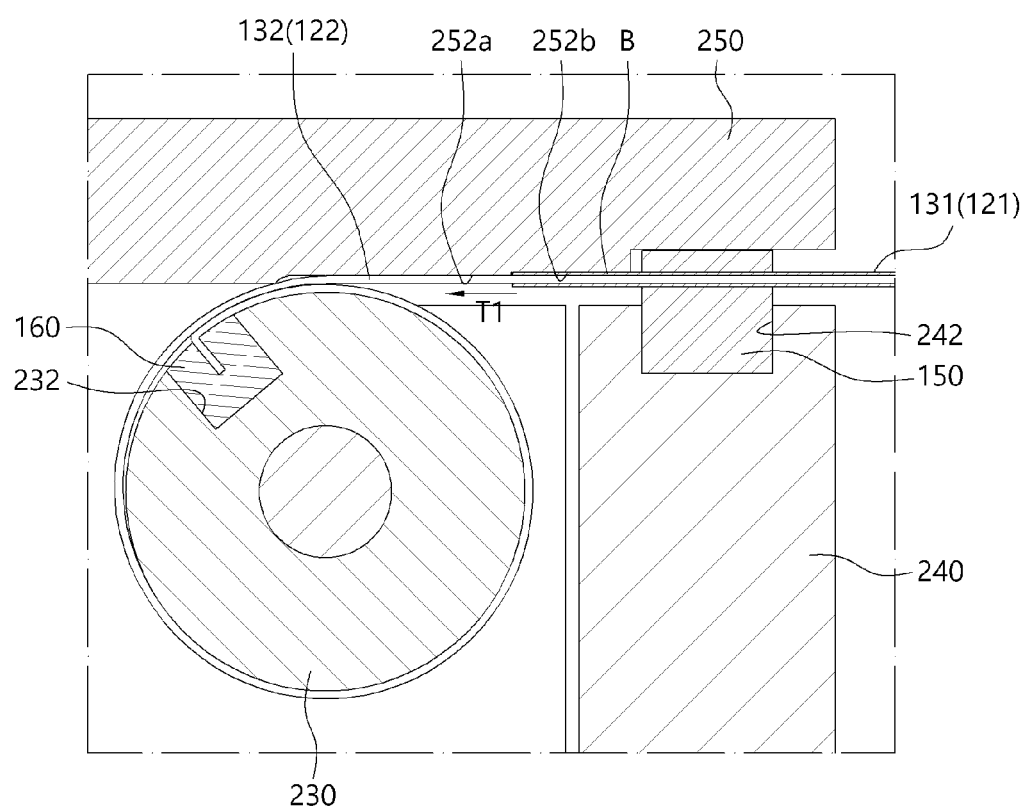
FIG. 9 is a view illustrating an operation state of a case in which a motor pulls the wire in FIG. 8.
Figure 10:
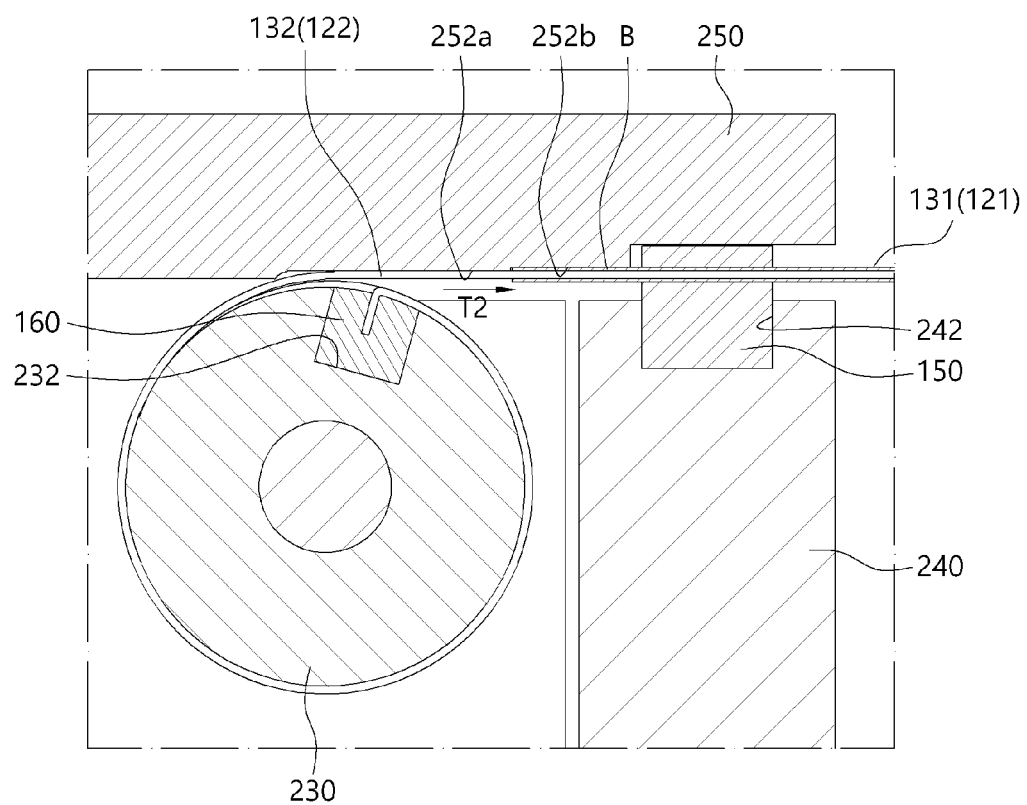
FIG. 10 is a view illustrating an operation state of a case in which the motor pushes the wire in FIG. 8.

Accordingly, as illustrated in FIGS. 9 and 10, in a state in which the wire holder 160 is installed in the first accommodation groove 232, in a case in which the driving roller 230 rotates in one direction or the opposite direction, the wire holder 160 to which the end portion of the wire 122 or 132 is fixed may also be rotated by the driving roller 230 to pull or push the wire 122 or 132.

In this case, one side of the arrangement hole 212 may be formed to be open so that the first accommodation groove 232 is exposed to the outside. Accordingly, in a case in which the first accommodation groove 232 is disposed to be positioned in the arrangement hole 212 formed to be open, the wire holder 160 may be easily installed in the first accommodation groove 232.

In addition, a seating groove 234 recessed inward in a circumferential direction may be formed in the driving roller 230 to accommodate a thickness of the wire 122 or 132. Accordingly, in a state in which a partial length of an entire length of the wire 122 or 132 passing through the sheath 121 or 131 is wound around the driving roller 230 at least one time along the seating groove 234, since the end portion of the wire 122 or 132 may be fixed to the wire holder 160, a force may be smoothly transmitted to the wire 122 or 132 by rotation.

In addition, even when the driving roller 230 rotates in one direction or the opposite direction to withdraw the wire 122 or 132 from the sheath 121 or 131, since the wire 122 or 132 is guided along the seating groove 234 so that a winding direction of the wire 122 or 132 is guided, a force may be smoothly transmitted to the wire 122 or 132.

In this case, the driving motor 220 may be driven in a forward or reverse direction through control of a control part, and the control part may be the control part 140 described above.

The weight measurement part 240 may be fixedly installed on one side of the main body 210, and a second accommodation groove 242 for accommodating the sheath holder 150 may be formed in one side. That is, the sheath holder 150, to which a partial length of the sheath 121 or 131 is fixedly coupled, may be detachably installed in the second accommodation groove 242.

In this case, the weight measurement part 240 may be a load cell, and the second accommodation groove 242 may be directly formed in one side of the load cell or may also be formed as a separated member fixedly coupled to the load cell.

As an example, in a case in which the sheath holder 150 is installed in the second accommodation groove 242, the weight measurement part 240 may be disposed on one side of the driving roller 230 so that the wire 122 or 132 passing through the sheath 121 or 131 and exposed to the outside is linearly disposed toward the wire holder 160.

Accordingly, in a state in which the sheath holder 150 is installed in the second accommodation groove 242 and the wire holder 160 is installed in the first accommodation groove 232, in a case in which the wire holder 160 is rotated by rotation of the driving roller 230 to provide a force to the wire 122 or 132, the weight measurement part 240 may measure a force applied to the sheath holder 150 and may measure a force of the sheath 121 or 131 using the force applied to the sheath holder 150.

In this case, since the force applied to the wire 122 or 132 and the force applied to the sheath 121 or 131 are the same according to a relationship of action and reaction, the force applied to the wire 122 or 132 can be easily measured by measuring the force applied to the sheath holder 150.

Accordingly, a force provided to the wire 122 or 132 through the driving motor 220 may be exactly controlled by control of the control part 140 on the basis of a magnitude of a load applied to the sheath holder 150.

Accordingly, in the power transmission system 100 for driving a robot joint described above, since a magnitude of a pulling force applied to the wire serving as the master cable and a magnitude of a pushing force applied to the wire serving as the slave cable may be properly controlled, a friction force generated between the wire serving as the slave cable and the sheath may be compensated for exactly.

In this case, the cable driving apparatus 200 for driving a robot joint according to one embodiment of the present invention may include a cover 250 so that, in a case in which a force is applied to the wire 122 or 132 in a second direction, in which the wire 122 or 132 is pushed into the sheath 121 or 131, by driving of the driving motor 220, the wire 122 or 132 is not bent and is exactly moved into the sheath 121 or 131 by the applied force.

That is, the cable driving apparatus 200 for driving a robot joint according to one embodiment of the present invention may include the cover 250 having a cover surface 251 which covers an upper portion of the first accommodation groove 232 and an upper portion of the second accommodation groove 242 at the same time in an initial state in which the wire holder 160 and the sheath holder 150 are respectively installed in the first accommodation groove 232 and the second accommodation groove 242, and the first accommodation groove 232 is positioned at an open portion of the arrangement hole 212.

Accordingly, since the wire holder 160 and the sheath holder 150 respectively installed in the first accommodation groove 232 and the second accommodation groove 242 are pressed by the cover surface 251, the wire holder 160 and the sheath holder 150 may be prevented from being separated from the first accommodation groove 232 and the second accommodation groove 242, respectively.

The cover 250 may also be detachably coupled to the main body 210, and alternatively, one side of the cover 250 may also be rotatably coupled to the main body 210.

In this case, as illustrated in FIG. 7, the cover surface 251 may include a guide groove 252 formed to be recessed so that a protruding portion B of the sheath 121 or 131 protruding toward the driving roller 230 from the sheath holder 150 and a part of the wire 122 or 132 exposed to the outside from an end portion of the protruding portion B of the sheath 121 or 131 are seated on the guide groove 252 at the same time in a state in which the sheath holder 150 is installed in the second accommodation groove 242.

That is, the guide groove 252 may include a first guide groove 252*a* for accommodating the protruding portion B of the sheath 121 or 131 and a second guide groove 252*b* for accommodating the wire 122 or 132 exposed to the outside from the end portion of the protruding portion B of the sheath 121 or 131, and the first guide groove 252*a* and the second guide groove 252*b* may be formed to be connected to each other.

In addition, a bottom surface of the first guide groove 252*a* and a bottom surface of the second guide groove 252*b* may be formed as a stepped surface.

Accordingly, as illustrated in FIG. 8, in a state in which the sheath holder 150 is installed in the second accommodation groove 242, the protruding portion B of the sheath 121 or 131 protruding from the sheath holder 150 toward the driving roller 230 may be connected to an end portion of the first accommodation groove 232.

Accordingly, in the cable driving apparatus 200 for driving a robot joint according to one embodiment of the present invention, even when a force is applied to the wire 122 or 132 in the second direction which is a direction in which the wire 122 or 132 is pushed into the sheath 121 or 131 by driving of the driving motor 220, in a state in which a movement direction of the wire 122 or 132 is restricted by the second guide groove 252*b*, since the wire 122 or 132 may directly move into the sheath 121 or 131 through the end portion of the protruding portion B of the sheath 121 or 131 seated on the first guide groove 252*a*, the wire 122 or 132 may be exactly moved into the sheath 121 or 131 without being bent even when the force is applied in the direction in which the wire 122 or 132 is pushed.

Accordingly, in the cable driving apparatus 200 for driving a robot joint according to one embodiment of the present invention, even when a force is applied to the wire 122 or 132 in the second direction which is the direction in which the wire 122 or 132 is pushed into the sheath 121 or 131 by driving of the driving motor 220, since there is no side effect such as loss of a force or bending of a wire in a process in which the wire 122 or 132 moves into the sheath 121 or 131, the weight measurement part 240 may exactly measure a force applied to the sheath holder 150.

As described above, in the cable driving apparatus 200 for driving a robot joint according to one embodiment of the present invention, according to the structure described above, in a state in which the sheath holder 150 is installed in the second accommodation groove 242, and the wire holder 160 is installed in the first accommodation groove 232, a pulling force may be exactly applied to the wire 122 or 132, and a pushing force may also be exactly applied to the wire 122 or 132 by driving of the driving motor 220.

Accordingly, the cable driving apparatus 200 for driving a robot joint according to one embodiment of the present invention may be employed as the driving unit 110a or 110b for implementing the power transmission system 100 for driving a robot joint.

Meanwhile, the power transmission system 100 for driving a robot joint described above may constitute an endoscopic surgery system, and in the power transmission system 100 for driving a robot joint, the cable driving apparatus 200 for driving a robot joint may be provided as the driving unit.

Figure 11:
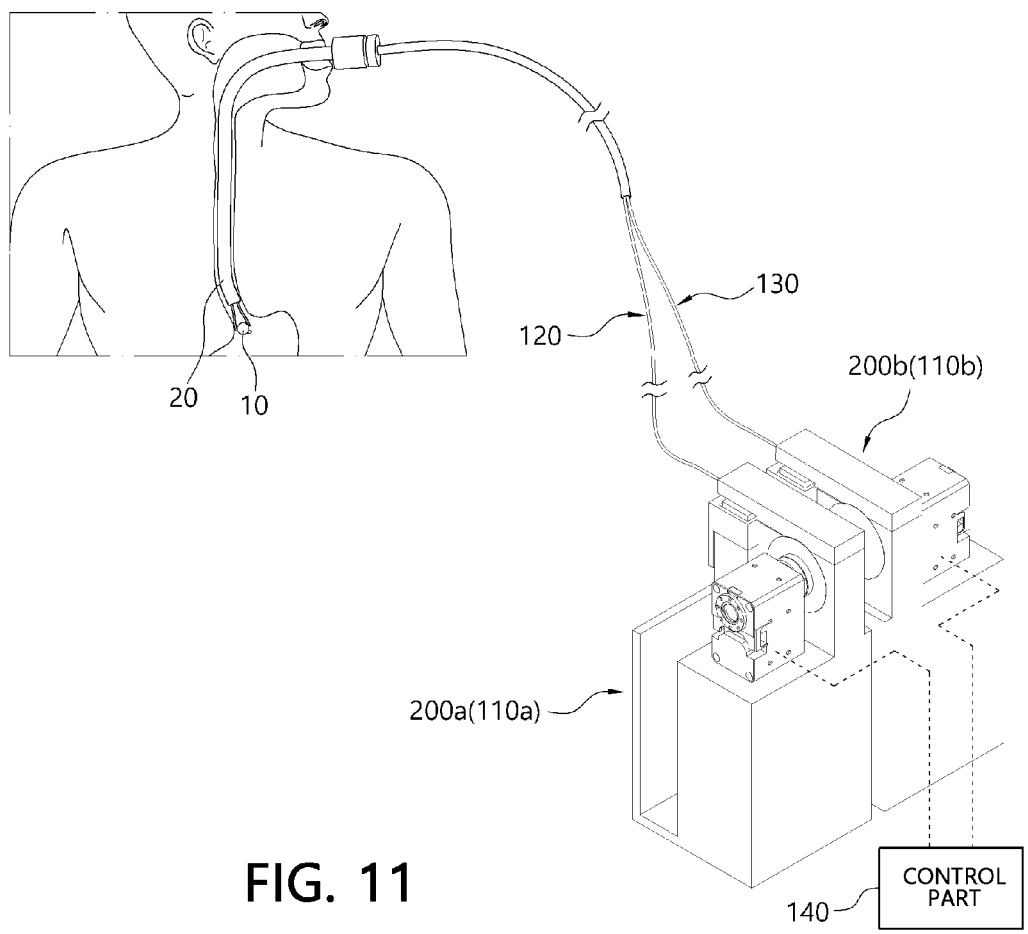
FIG. 11 is a schematic view illustrating a state in which the power transmission system for driving a robot joint according to one embodiment of the present invention is applied to an endoscopic surgery system.

As an example, as illustrated in FIG. 11, a power transmission system 100 for driving a robot joint may include a first driving unit 110a, a second driving unit 110b, a first force transmission part 120 including a first sheath 121 and a first wire 122, and a second force transmission part 130 including a second sheath 131 and a second wire 132, and the cable driving apparatus 200 for driving a robot joint described above may be provided as each of the first driving unit 110a and the second driving unit 110b.

In this case, the first force transmission part 120 including the first sheath 121 and the first wire 122 and the second force transmission part 130 including the second sheath 131 and the second wire 132 may be employed without change, and the cable driving apparatus 200 for driving a robot joint described above may be employed as the cable driving apparatus 200 for driving a robot joint without change. Accordingly, detailed descriptions thereof will be omitted.

In this case, the first force transmission part 120 and the second force transmission part 130 may be inserted into a protection tube 20 intubated into a patient's body through a patient's mouth, one end of the first wire 122 may be connected to a driving joint of a robot which is a control target object 10, the other end of the first wire 122 may be fixed to a wire holder 160 provided in a first cable driving apparatus 200a for driving a robot joint, one end of the second wire 132 may be connected to target object 10 of the robot, the other end of the second wire 132 may be fixed to a wire holder 160 provided in a second cable driving apparatus 200b for driving a robot joint. In this case, an endoscope may be fixed to the driving joint of the robot which is the control target object 10.

In this state, an operator may operate the first cable driving apparatus 200a for driving a robot joint and the second cable driving apparatus 200b for driving a robot joint using a control part 140 to push the second wire 132 while pulling the first wire 122 or to push the first wire 122 while pulling the second wire 132.

Accordingly, since the driving joint of the robot which is the control target object 10 may exactly move to a position in a direction desired by the operator, and the endoscope fixed to the control target object 10 may also exactly move to a position in a direction desired by the operator, the accuracy of a procedure can be improved.

In addition, since the wire holder 160 and a sheath holder 150 may be detachably installed in a first accommodation groove 232 and a second accommodation groove 242, respectively, the wire holder 160 and the sheath holder 150 together with the first force transmission part 120 and the second force transmission part 130 may be simply removed and replaced with unused products, and the first cable driving apparatus 200a for driving a robot joint and the second cable driving apparatus 200b for driving a robot joint which provide driving forces may be simply reused without risk of contamination.

Meanwhile, as an example of an application to which the power transmission system 100 for driving a robot joint or the power transmission system 100 for driving a robot joint including the cable driving apparatus 200 for driving a robot joint is applied, the endoscopic surgery system is illustrated, but the present invention is not limited thereto, may be applied to any robot arm performing grip work or any driving joint of a robot for driving an robot arm, and may be widely applied to medical, household, and industrial fields, and the like.

Figure 12:
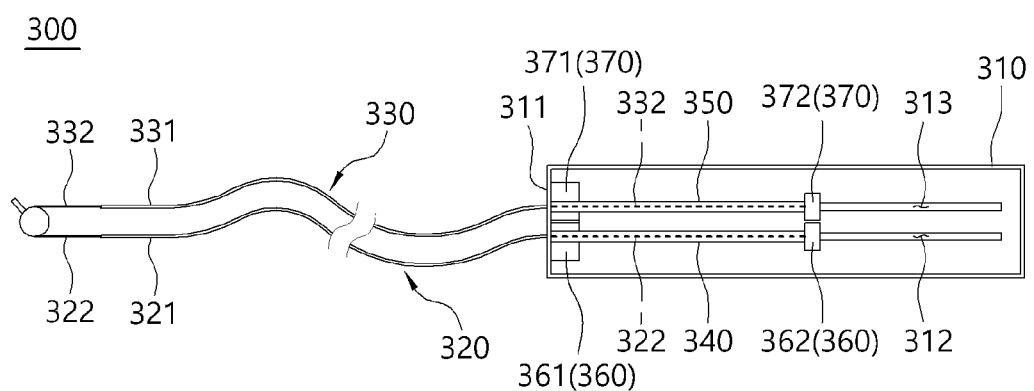
FIG. 12 is a schematic view illustrating a power transmission system for driving a robot joint according to another embodiment of the present invention.
Figure 13:
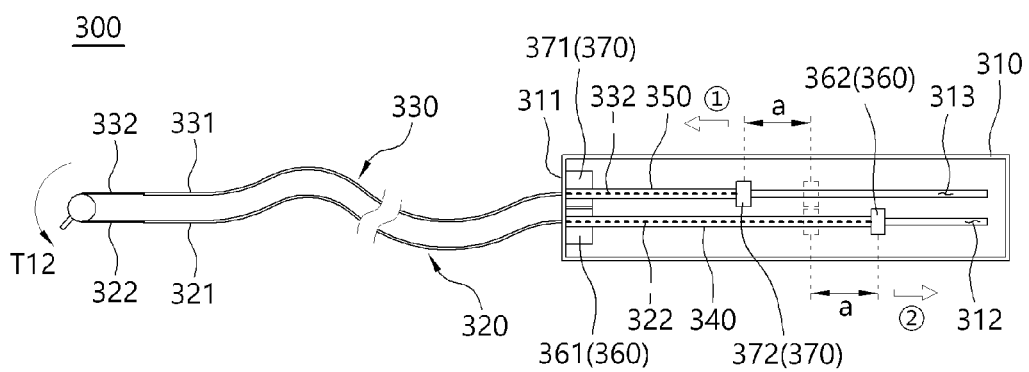
FIG. 13 is a view illustrating an operation state of that of FIG. 12.

FIG. 12 is a schematic view illustrating a power transmission system for driving a robot joint according to another embodiment of the present invention, and FIG. 13 is a view illustrating an operation state of that of FIG. 12.

Referring to FIGS. 12 and 13, a power transmission system 300 for driving a robot joint according to another embodiment of the present invention realizes a double input sheath-tendon power transmission mechanism and includes a body part 310, a driving part including a first driving unit 360 and a second driving unit 370, a first force transmission part 320, a second force transmission part 330, a first elastic part 340, and a second elastic part 350.

The body part 310 may accommodate the first driving unit 360, the second driving unit 370, the first elastic part 340, and the second elastic part 350. The body part 310 may be formed of a plastic or metal material or one of various materials having corrosion resistance while having rigidity.

The first driving unit 360 may be disposed in the body part 310. The first driving unit 360 may include a first driving motor 361 and a first moving part 362.

The first driving motor 361 may be installed in the body part 310. The first driving motor 361 may receive power to generate a driving force.

The first moving part 362 may receive the driving force of the first driving motor 361 to move linearly. For example, the first moving part 362 may be moved in a first direction ① or second direction ② which is opposite to the first direction ①, by the driving force of the first driving motor 361.

According to one embodiment of the present invention, the body part 310 may include a first guide hole 312 which guides the first moving part 362. The first moving part 362 may move along the first guide hole 312 in the first direction ① or second direction ②.

The second driving unit 370 may be disposed in the body part 310. The second driving unit 370 may include a second driving motor 371 and a second moving part 372.

The second driving motor 371 may be installed in the body part 310. The second driving motor 371 may receive power to generate a driving force.

The second moving part 372 may receive the driving force of the second driving motor 371 to move linearly. For example, the second moving part 372 may be moved in the first direction ① or second direction ②, which is opposite to the first direction ①, by the driving force of the second driving motor 371.

According to one embodiment of the present invention, the body part 310 may include a second guide hole 313 which guides the second moving part 372. The second guide hole 313 may be formed to be parallel to the first guide hole 312. The second moving part 372 may move along the second guide hole 313 in the first direction ① or second direction ②.

In each of the first force transmission part 320 and the second force transmission part 330, a sheath-tendon mechanism in which a tendon is inserted into a sheath to be moved in a longitudinal direction therein may be employed.

The first force transmission part 320 may include a first sheath 321 and a first wire 322. The first sheath 321 may be formed to have a predetermined length, flexibility, and a hollow shape. The first wire 322 may be inserted into the first sheath 321. The first wire 322 may be inserted into the first sheath 321 so that both end portions of the first wire 322 are exposed to the outside of the first sheath 321. One end of both of the end portions of the first wire 322 may be fixed to a joint 10 of a robot. The other end of both of the end portions of the first wire 322 may pass through one side 311 of the body part 310 and may be fixed to the first moving part 362 of the first driving unit 360.

The second force transmission part 330 may include a second sheath 331 and a second wire 332. The second sheath 331 may be formed to have a predetermined length, flexibility, and a hollow shape. The second wire 332 may be inserted into the second sheath 331. The second wire 332 may be inserted into the second sheath 331 so that both end portions of the second wire 332 are exposed to the outside of the second sheath 331. One end of both of the end portions of the second wire 332 may be fixed to the joint 10 of the robot. The other end of both of the end portions of the second wire 332 may pass through the one side 311 of the body part 310 and may be fixed to the second moving part 372 of the second driving unit 370.

According to another embodiment of the present invention, a first wire hole through which the first wire 322 passes and a second wire hole through which the second wire 332 passes may be formed in the one side 311 of the body part 310.

According to another embodiment of the present invention, the joint 10 of the robot may be a driving joint for driving a finger or wrist of a robot arm in a robot.

In addition, each of the first sheath 321 and the second sheath 331 may be a coil shaped tube formed of a metal material to withstand tension applied to each of the first wire 322 and the second wire 332, to maintain an overall shape, and to have flexibility. However, the shape and the material of each of the first sheath 321 and the second sheath 331 are not limited thereto, and any shape and any material employed for a sheath in a known sheath-tendon mechanism may be applied thereto.

In addition, the power transmission system 300 for driving a robot joint according to another embodiment of the present invention may further include a control part for controlling overall operations of the first driving unit 360 and the second driving unit 370, and the control part may control driving of the first driving unit 360 and the second driving unit 370 on the basis of an input signal of a user. In addition, the control part may control a magnitude of a force provided to the first wire 322 from the first driving unit 360 and a magnitude of a force provided to the second wire 332 from the second driving unit 370 on the basis of the input signal of the user. The control part may control the first driving unit 360 to provide a force to the first wire 322 in the first direction ① and control the second driving unit 370 to provide a force to the second wire 332 in the second direction ②.

In addition, the first force transmission part 320 and the second force transmission part 330 may be connected to each other by the joint 10 of the robot, and in a case in which a driving force is provided to the first wire 322 from the first driving unit 360, or a driving force is provided to the second wire 332 from the second driving unit 370 through control of the control part, the first wire 322 and the second wire 332 may be respectively moved in the first sheath 321 and the second sheath 331 in longitudinal directions. Accordingly, the joint 10 of the robot may be rotated or moved to a position desired by the user.

According to another embodiment of the present invention, unlike a conventional double input sheath-tendon mechanism, the first driving unit 360 and the second driving unit 370 may provide a driving force to the first force transmission part 320 and provide a driving force to the second force transmission part 330, respectively, at the same time, and a magnitude of the driving force provided to the first force transmission part 320 from the first driving unit 360 and a magnitude of the driving force provided to the second force transmission part 330 from the second driving unit 370 may be controlled by the control part.

In the power transmission system 300 for driving a robot joint according to another embodiment of the present invention, as illustrated in FIG. 13, in a case in which the first driving unit 360 provides a force to the first wire 322 in the first direction ①, the second driving unit 370 may provide a force to the second wire 332 in the second direction ②. Similarly, in the power transmission system 300 for driving a robot joint according to another embodiment of the present invention, in a case in which the second driving unit 370 provides a force to the second wire 332 in the first direction ①, the first driving unit 360 may provide a force to the first wire 322.

In addition, in the first wire 122 and the second wire 132, a role of a master cable and a role of a slave cable may be interchanged according to a direction of a force provided from the first driving unit 360 and a direction of a force provided from the second driving unit 370. That is, in a case in which the first wire 322 is moved by a first length a in the first direction ①, and the second wire 332 is moved by the first length a in the second direction ②, the first wire 322 may serve as the master cable, and the second wire 332 may serve as the slave cable. Conversely, in a case in which the first wire 322 is moved by the first length a in the second direction ②, and the second wire 332 is moved by the first length a in the first direction ①, the second wire 332 may serve as the master cable, and the first wire 322 may serve as the slave cable.

In the power transmission system 300 for driving a robot joint according to another embodiment of the present invention, by providing a pulling force to the wire serving as the master cable using the driving unit and providing an actively pushing force to the wire serving as the slave cable using the driving unit at the same time, a friction force generated due to contact between the wire and the sheath in a process in which the wire serving as the slave cable moves in the sheath may be compensated for. Accordingly, in the power transmission system 300 for driving a robot joint according to another embodiment of the present invention, even when the wire serving as the master cable is pulled using a small force, target object 10 of the robot may be moved to a desired position. For example, when a magnitude of a force provided to the first wire 322 by the first driving unit 360 in the second direction ② is the same as a magnitude of a friction force generated between the first wire 322 and the first sheath 321 in a process in which the first wire 322 is moved in the longitudinal direction of the first sheath 321 by the first driving unit 360 and a magnitude of a force T12 for moving the joint 10 of the robot, the joint 10 of the robot may be moved to a position desired by a worker.

As described above, in the power transmission system 300 for driving a robot joint according to another embodiment of the present invention, as a driving force, which actively pushes the wire, is provided to the wire serving as the slave cable using the driving unit to cancel a friction force generated between the wire serving as the slave cable and the sheath, even when a small magnitude of a driving force is provided to the wire serving as the master cable, a power transmission amount at a level which is greater than or equal to that in a conventional case can be obtained.

In addition, according to the present invention, since a friction force generated by the slave cable is canceled to prevent or reduce backlash at the slave cable, there is an advantage of improving control precision.

The first elastic part 340 may wrap the other end of the first wire 322. For example, the other end of the first wire 322 may be a portion, which is disposed in the body part 310, of an entire portion of the first wire 322. One end of the first elastic part 340 may be fixed to an inner surface of the body part 310, and the other end of the first elastic part 340 may be fixed to the first moving part 362 of the first driving unit 360. The first elastic part 340 may be formed in a tube shape. The first elastic part 340 may be formed of one of various materials having elasticity while maintaining substantially a tube shape.

As the first moving part 362 moves in the first direction ①, the first elastic part 340 may contract, and as the first moving part 362 moves in the second direction ②, the first elastic part 340 may extend. Even when the first wire 322 is moved in the first direction ① or second direction ② by the first moving part 362, a state in which the first elastic part 340 wraps the first wire 322 may be maintained. Accordingly, the first elastic part 340 may prevent the first wire 322 from being loosened in the body part 310.

The second elastic part 350 may wrap the second wire 332 disposed in the body part 310. One end of the second elastic part 350 may be fixed to the inner surface of the body part 310, and the other end of the second elastic part 350 may be fixed to the second moving part 372 of the second driving unit 370. The second elastic part 350 may be formed in a tube shape. The second elastic part 350 may be formed of one of various materials having elasticity while maintaining substantially a tube shape. In addition, the second elastic part 350 may be disposed to be parallel to the first elastic part 340.

As the second moving part 372 moves in the first direction ①, the second elastic part 350 may contract, and as the second moving part 372 moves in the second direction ②, the second elastic part 350 may extend. Even when the second wire 332 is moved in the first direction ① or second direction ② by the second moving part 372, a state in which the second elastic part 350 wraps the second wire 332 may be maintained. Accordingly, the second elastic part 350 may prevent the second wire 332 from being loosened in the body part 310.

Figure 14:
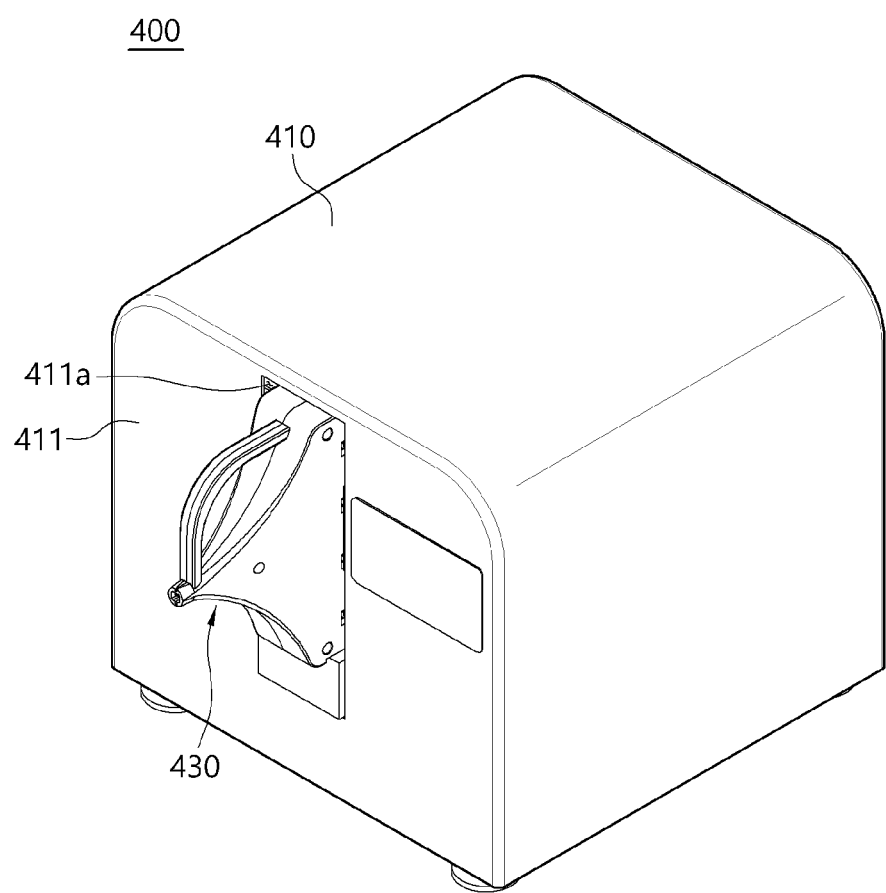
FIG. 14 is a perspective view illustrating a cartridge type power transmission system for driving a robot joint according to still another embodiment of the present invention.
Figure 15:
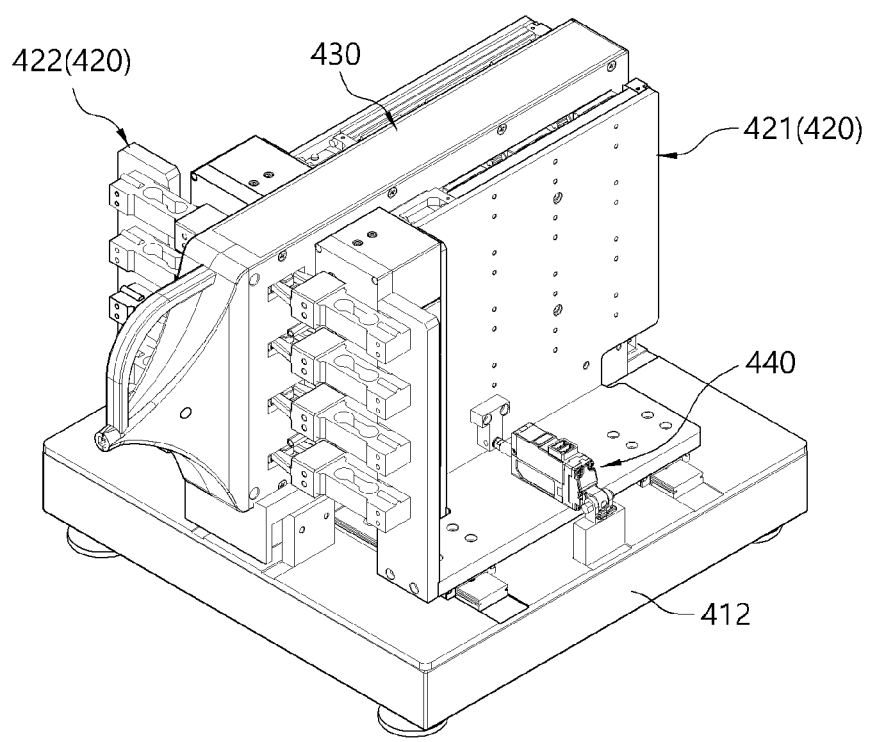
FIG. 15 is a schematic perspective view illustrating a structure of the cartridge type power transmission system for driving a robot joint according to still another embodiment of the present invention.
Figure 16:
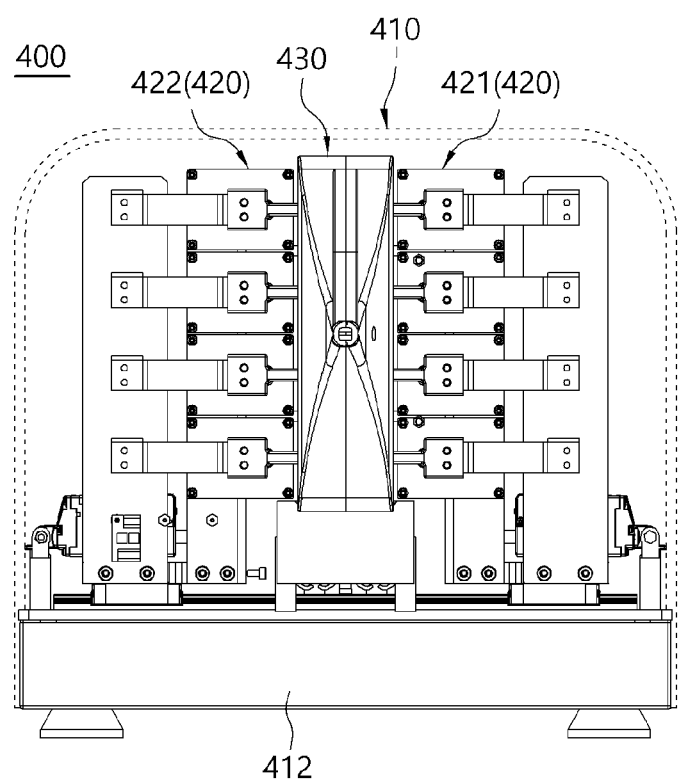
FIG. 16 is a schematic front view illustrating the structure of the cartridge type power transmission system for driving a robot joint according to still another embodiment of the present invention.
Figure 17:
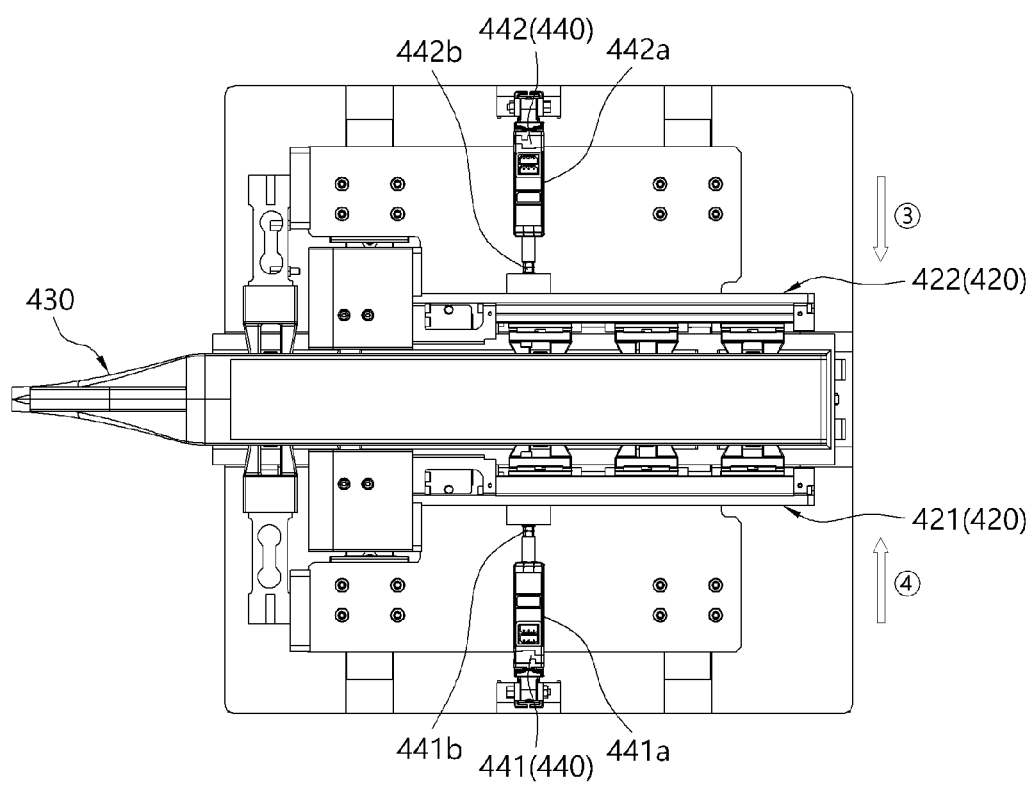
FIG. 17 is a schematic plan view illustrating the structure of the power transmission system for driving a robot joint according to still another embodiment of the present invention.
Figure 18:
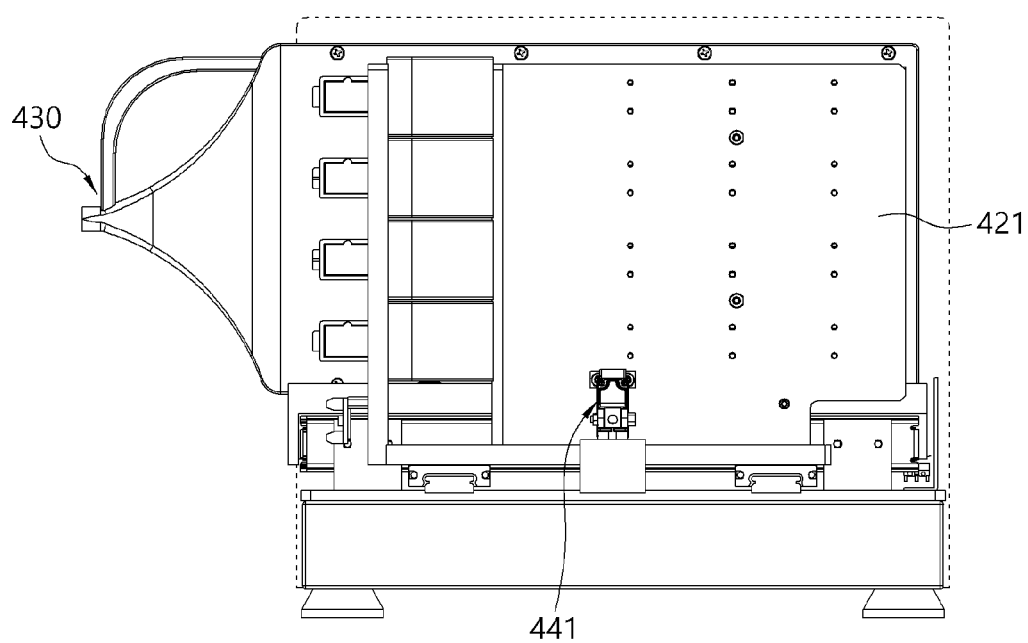
FIG. 18 is a schematic side view illustrating the structure of the power transmission system for driving a robot joint according to still another embodiment of the present invention.

FIG. 14 is a perspective view illustrating a cartridge type power transmission system for driving a robot joint according to still another embodiment of the present invention, FIG. 15 is a schematic perspective view illustrating a structure of the cartridge type power transmission system for driving a robot joint according to still another embodiment of the present invention, FIG. 16 is a schematic front view illustrating the structure of the cartridge type power transmission system for driving a robot joint according to still another embodiment of the present invention, FIG. 17 is a schematic plan view illustrating the structure of the cartridge type power transmission system for driving a robot joint according to still another embodiment of the present invention, and FIG. 18 is a schematic side view illustrating the structure of the cartridge type power transmission system for driving a robot joint according to still another embodiment of the present invention.

Referring to FIGS. 14 to 18, a cartridge type power transmission system 400 for driving a robot joint according to still another embodiment of the present invention may include a housing 410, a first driving part 420, and a cartridge 430.

The housing 410 may accommodate the first driving part 420, the cartridge 430, and the second driving part 440 which will be described below. The housing 410 may be formed of a plastic or metal material. In addition, the housing 410 is not limited to being formed of the plastic or metal material and may be formed of one of various material having corrosion resistance while having rigidity. An insertion hole 411a through which the cartridge 430 is inserted into the housing 410 may be formed in one side 411 of the housing 410. In addition, a display, which displays a state of the cartridge type power transmission system 400 for driving a robot joint, may be disposed on the one side 411 of the housing 410.

The first driving part 420 may be disposed in the housing 410. The first driving part 420 may move linearly in a first direction ① (see FIG. 13) or second direction ② (see FIG. 13). The first driving part 420 may be provided as a plurality of first driving parts 420. The plurality of first driving parts 420 may include one first driving part 421 of the plurality of first driving parts facing one side surface of the cartridge 430 and another first driving part 422 of the plurality of first driving parts facing the other side surface of the cartridge 430. The another first driving part 422 of the plurality of first driving parts may be symmetrically disposed with respect to the one first driving part 421 of the plurality of first driving parts with the cartridge 430 interposed therebetween. The one first driving part 421 of the plurality of first driving parts may be provided as four first driving parts 421, and the another first driving part 422 of the plurality of first driving parts may be provided as four first driving parts 422. However, one first driving part 421 of the plurality of first driving parts and the another first driving part 422 of the plurality of first driving parts are not limited to being provided as four first driving parts 421 and four first driving parts 422, respectively, and the number thereof may vary to be two or six. The first driving part 420 will be described with reference to the drawings below.

The cartridge 430 may be inserted into the housing 410 through the insertion hole 411a. The cartridge 430 may include force transmission parts 439 (see FIG. 21) and elastic parts 438 for implementing a double input sheath-tendon power transmission mechanism. The cartridge 430 will be described with reference to the drawings below.

The cartridge type power transmission system 400 for driving a robot joint according to still another embodiment of the present invention may further include a second driving part 440.

The second driving part 440 may move the first driving part 420 in a third direction ③ or fourth direction ④ which is opposite to the third direction ③, so that the first driving part 420 is connected to or separated from the cartridge 430. The third direction ③ may be a direction perpendicular to a first direction ①. The second driving part 440 may be provided as a plurality of second driving parts 440. The plurality of second driving parts 440 may include one second driving part 441, which is disposed at a side opposite to the cartridge 430 with the one first driving part 421 of the plurality of first driving parts interposed between the one second driving part 441 and the cartridge 430, of the plurality of second driving parts and another second driving part 442, which is disposed at a side opposite to the cartridge 430 with the another first driving part 422 of the plurality of first driving parts interposed between the another second driving part 442 and the cartridge 430, of the plurality of second driving parts.

The one second driving part 441 of the plurality of second driving parts may include a second motor 441a and a connection part 441b. The second motor 441a may be disposed on a lower surface 412 of the housing 410. The connection part 441b may be connected to the second motor 441a and moved linearly in the third direction ③ or fourth direction ④ by a driving force of the second motor 441a. The connection part 441b may be connected to the one first driving part 421 of the plurality of first driving parts.

The one second driving part 441 of the plurality of second driving parts may move the one first driving part 421 of the plurality of first driving parts in the fourth direction ④ to connect the one first driving part 421 of the plurality of first driving parts to the cartridge 430. In addition, the one second driving part 441 of the plurality of second driving parts may move the one first driving part 421 of the plurality of first driving parts in the third direction ③ to separate the one first driving part 421 of the plurality of first driving parts from the cartridge 430.

The another second driving part 442 of the plurality of second driving parts may include a second motor 442a and a connection part 442b. The second motor 442a may be disposed on the lower surface 412 of the housing 410. The connection part 442b may be connected to the second motor 442a and moved linearly in the third direction ③ or fourth direction ④ by a driving force of the second motor 442a. The connection part 442b may be connected to the another first driving part 422 of the plurality of first driving parts.

The another second driving part 442 of the plurality of second driving parts may move the another first driving part 422 of the plurality of first driving parts in the third direction ③ to connect the another first driving part 422 of the plurality of first driving parts to the cartridge 430. In addition, the another second driving part 442 of the plurality of second driving parts may move the another first driving part 422 of the plurality of first driving parts in the fourth direction ④ to separate the another first driving part 422 of the plurality of first driving parts from the cartridge 430.

In a process in which the cartridge 430 is inserted into or separated from the housing 410, the second driving part 440 may control whether the first driving part 420 is connected to the cartridge 430.

According to still another embodiment of the present invention, the one second driving part 441 of the plurality of second driving parts and the another second driving part 442 of the plurality of second driving parts may be driven at the same time.

Figure 19:
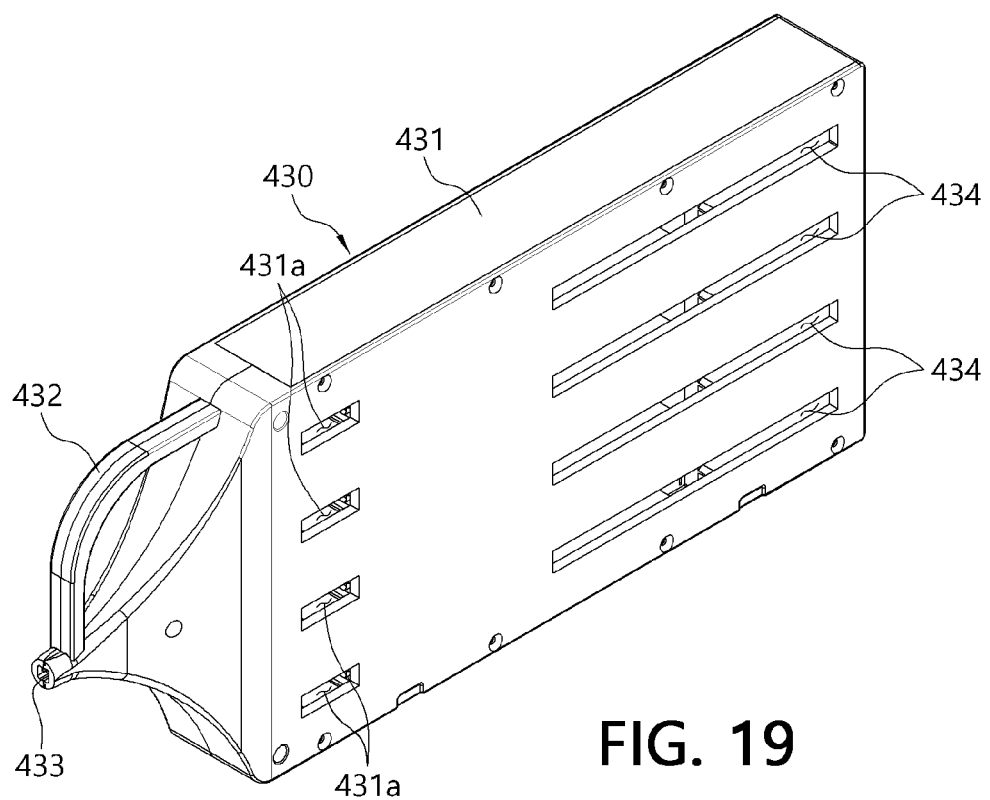
FIG. 19 is a perspective view illustrating a cartridge of the cartridge type power transmission system for driving a robot joint according to still another embodiment of the present invention.
Figure 20:
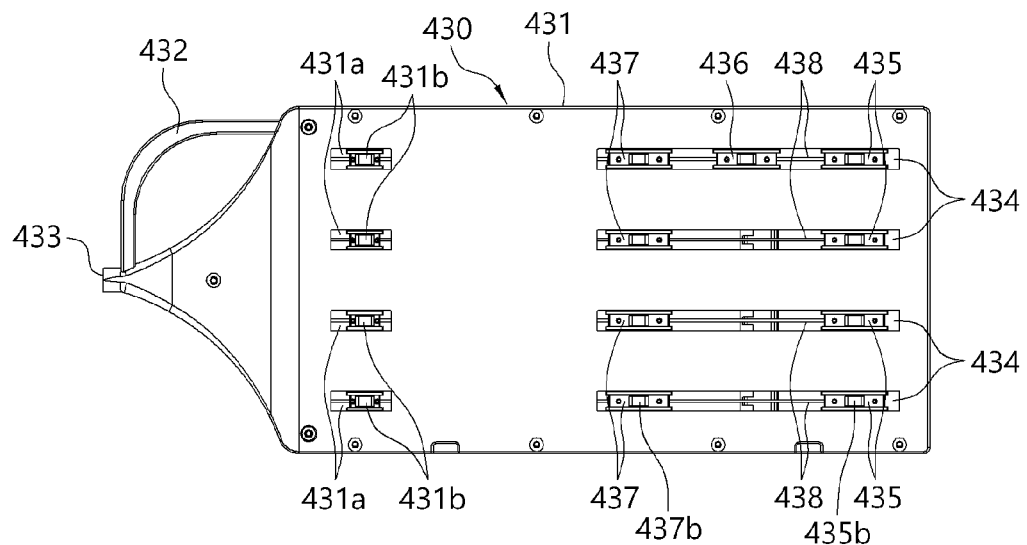
FIG. 20 is a side view illustrating the cartridge of the cartridge type power transmission system for driving a robot joint according to still another embodiment of the present invention.
Figure 21:
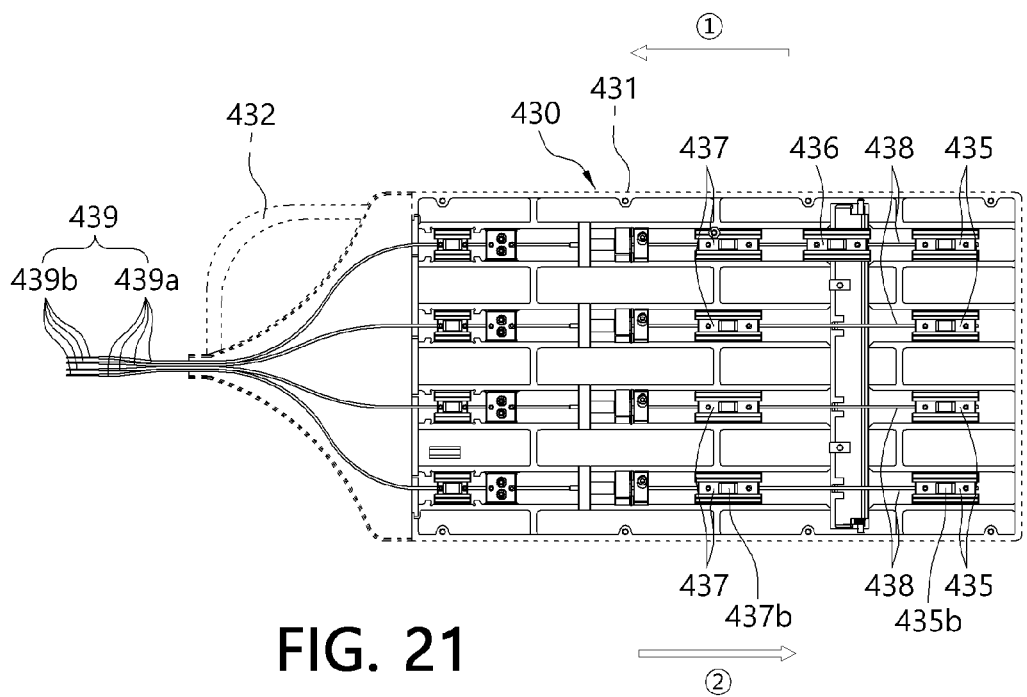
FIG. 21 is a schematic view illustrating a structure of the cartridge of the cartridge type power transmission system for driving a robot joint according to still another embodiment of the present invention.
Figure 22:
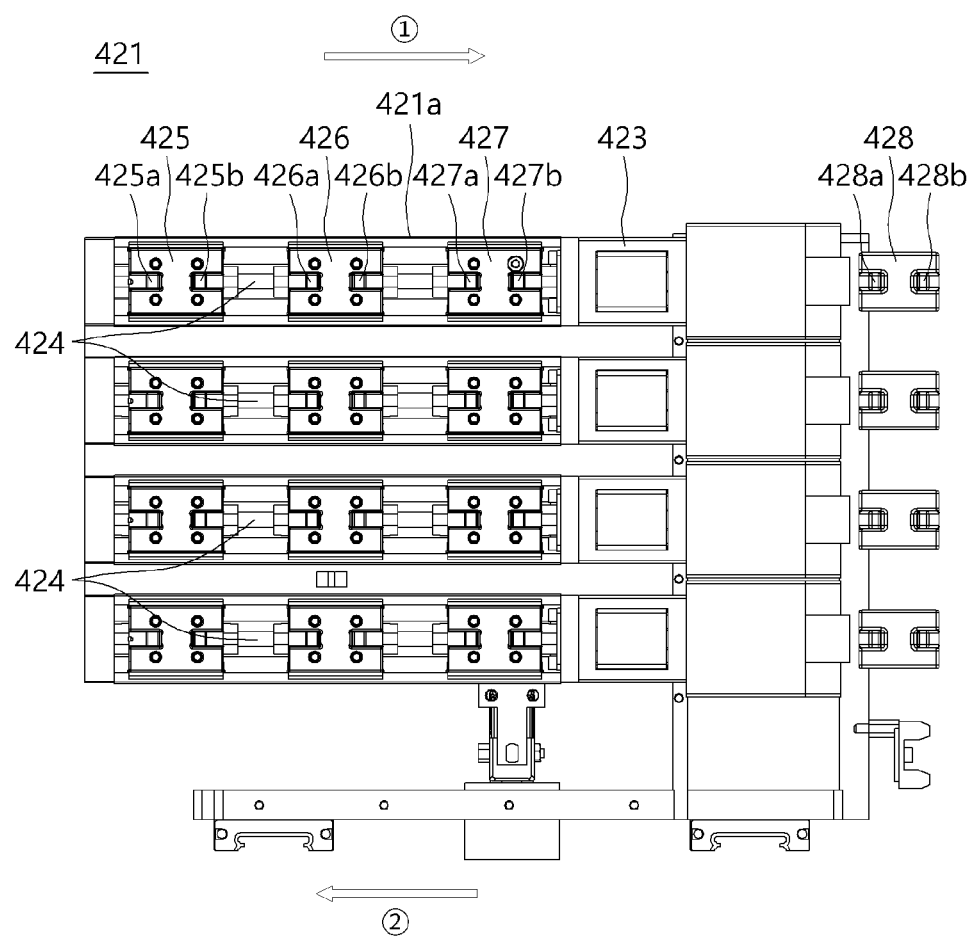
FIG. 22 is a side view illustrating a first driving part of the cartridge type power transmission system for driving a robot joint according to still another embodiment of the present invention.

FIG. 19 is a perspective view illustrating the cartridge of the cartridge type power transmission system for driving a robot joint according to still another embodiment of the present invention, FIG. 20 is a side view illustrating the cartridge of the cartridge type power transmission system for driving a robot joint according to still another embodiment of the present invention, FIG. 21 is a schematic view illustrating a structure of the cartridge of the cartridge type power transmission system for driving a robot joint according to still another embodiment of the present invention, and FIG. 22 is a side view illustrating the first driving part of the cartridge type power transmission system for driving a robot joint according to still another embodiment of the present invention.

Referring to FIGS. 19 to 22, the cartridge 430 of the cartridge type power transmission system for driving a robot joint according to still another embodiment of the present invention may include a case 431, moving parts 435, 436, and 437, the force transmission parts 439, and the elastic parts 438.

The case 431 may accommodate the moving parts 435, 436, and 437, the force transmission parts 439, and the elastic parts 438. The case 431 may be formed of a plastic or metal material. In addition, the case 431 is not limited to being formed in the plastic or metal materials and may be formed of one of various materials having corrosion resistance while having rigidity. The case 431 may include a handle part 432 gripped by a hand of a user or a tool.

The case 431 may include a guide hole 434 which guides the moving parts 435, 436, and 437. The guide hole 434 may be formed in a slit shape. The guide hole 434 may be provided as a plurality of guide holes 434. The plurality of guide holes 434 may be formed to be parallel to each other.

The moving parts 435, 436, and 437 may be accommodated in the case 431. The moving parts 435, 436, and 437 may be connected to the first driving part 420. The moving parts 435, 436, and 437 may receive a driving force of the first driving part 420 to be moved linearly in a first direction ① or second direction ②. The moving parts 435, 436, and 437 may be exposed to the outside of the case 431 through the guide holes 434. The moving parts 435, 436, and 437 may include a first moving part 435, a second moving part 436, and a third moving part 437. The first moving part 435, the second moving part 436, and the third moving part 437 may be arranged to be parallel to each other.

The force transmission parts 439 may include sheaths 439a and wires 439b.

The sheath 439a may be formed to have a predetermined length, flexibility, and a hollow shape. One portion of the sheath 439a may be accommodated in the case 431, and the other portion of the sheath 439a may be exposed to the outside of the case 431.

In addition, the sheath 439a may be similar to or the same as each of the first sheath 321 and the second sheath 331 of the embodiment described above.

The wire 439b may be inserted into the sheath 439a. One end of the wire 439b may be fixed to a joint 10 of a robot (see FIG. 12), and the other end of the wire 439b may be fixed to the first moving part 435. The other end of the wire 439b may be moved in the first direction ① or second direction ② by movement of the first moving part 435.

In addition, the wire 439b may be the same as or similar to each of the first wire 322 and the second wire 332 of the embodiment described above.

The elastic part 438 may be disposed in the case 431. One end of the elastic part 438 may be fixed to the case 431, and the other end of the elastic part 438 may be fixed to the first moving part 435. The elastic part 438 may extend in the first direction ① or contract in the second direction ② by movement of the first moving part 435.

In addition, according to still another embodiment of the present invention, the elastic part 438 may be fixed to the second moving part 436 and the third moving part 437. In addition, according to still another embodiment of the present invention, the elastic part 438 may pass through the second moving part 436 and the third moving part 437.

In addition, the elastic part 438 may be the same as or similar to the elastic part 438 of the embodiment described above.

The first driving part 421 of the cartridge type power transmission system for driving a robot joint according to still another embodiment of the present invention may include driving body parts 421a, first motors 423, and detachable parts 425, 426, and 427.

The driving body part 421a may be moved in the third direction ③ or fourth direction ④ in the housing 410 (see FIG. 16) by a driving force of the second driving part 440. The driving body part 421a may be coupled to the connection part 441b (see FIG. 17) of the second driving part 440.

The first motor 423 may be disposed on the driving body part 421a.

The detachable parts 425, 426, and 427 may be disposed on the driving body part 421a. The detachable parts 425, 426, and 427 may be connected to the first motor 423. The detachable parts 425, 426, and 427 may be moved linearly in the first direction ① or second direction ② by a driving force of the first motor 423. The detachable parts 425, 426, and 427 may be detachably coupled to the moving parts 435, 436, and 437.

The detachable parts 425, 426, and 427 may include protrusions 425a, 425b, 426a, 426b, 427a, and 427b protruding from outer surfaces of the detachable parts 425, 426, and 427. In addition, the moving parts 435, 436, and 437 may include detachable grooves 435b, 436b, and 437b into which the protrusions 425a, 425b, 426a, 426b, 427a, and 427b are inserted.

The detachable parts 425, 426, and 427 may include a first detachable part 425, a second detachable part 426, and a third detachable part 427. The first detachable part 425, the second detachable part 426, and the third detachable part 427 may be arranged to be parallel to each other.

As the protrusions 425a and 425b of the first detachable part 425 are inserted into or separated from the detachable groove 435b of the first moving part 435, the first detachable part 425 may be detachably coupled to the first moving part 435.

As the protrusions 426a and 426b of the second detachable part 426 are inserted into or separated from the detachable groove 436b of the second moving part 436, the second detachable part 426 may be detachably coupled to the second moving part 436.

As the protrusions 427a and 427b of the third detachable part 427 are inserted into or separated from the detachable groove 437b of the third moving part 437, the third detachable part 427 may be detachably coupled to the third moving part 437.

In addition, the cartridge 430 may further include first fixing parts 431b. The first fixing part 431b may be exposed at a side surface of the case 431 through a fixing hole 431a formed in the side surface of the case 431. In addition, the first driving part 420 may include second fixing parts 428. The second fixing part 428 may include fixing protrusions 428a and 428b. In addition, a fixing groove corresponding to the fixing protrusions 428a and 428b may be formed in the first fixing part 431b. The fixing protrusions 428a and 428b of the second fixing part 428 may be inserted into the fixing groove of the first fixing part 431b to firmly couple the first driving part 420 and the cartridge 430.

The detachable parts 425, 426, and 427 may receive a driving force of the first motor 423 to move in the first direction ① or second direction ②. After the moving parts 435, 436, and 437 are respectively connected to the detachable parts 425, 426, and 427, the moving parts 435, 436, and 437 may move in the first direction ① or second direction ② with the detachable parts 425, 426, and 427. In addition, the wire 439b may move in the first direction ① or second direction ② with the moving parts 435, 436, and 437. The joint 10 (see FIG. 12) of the robot connected to the wire 439b may be driven by movement of the wire 439b.

While the embodiments of the present invention have been described above, the spirit of the present invention is not limited to the embodiments proposed in this specification, and the other embodiments may be easily suggested by adding, changing and the deleting components by those skilled in the art and will fall within the spiritual range of the present invention.

The invention claimed is:

1. A power transmission system for driving a robot joint, which is a cable power transmission system for driving a joint of a robot, the power transmission system comprising:
   a driving part including a first driving unit and a second driving unit;
   a first force transmission part including a first sheath formed to have a predetermined length, flexibility, and a hollow shape and a first wire which is inserted into the first sheath and of which one end is fixed to a joint of a robot and the other end is connected to the first driving unit; and
   a second force transmission part including a second sheath formed to have a predetermined length, flexibility, and a hollow shape and a second wire which is inserted into the second sheath and of which one end is fixed to the joint of the robot and the other end is connected to the second driving unit,
   wherein, in a case in which the first driving unit provides a force to the first wire in a first direction, the second driving unit provides a force to the second wire in a second direction opposite to the first direction.

2. The power transmission system of claim 1, wherein:
   in a case in which the first driving unit applies a force to the first wire in a direction in which the first wire is pulled, the second driving unit provides a force to the second wire in a direction in which the second wire is pushed; and
   in a case in which the second driving unit applies a force to the second wire in a direction in which the second wire is pulled, the first driving unit provides a force to the first wire in a direction in which the first wire is pushed.

3. The power transmission system of claim 1, wherein, in a case in which the first driving unit provides a force to the first wire in a direction in which the first wire is pulled and the second driving unit provides a force to the second wire in a direction in which the second wire is pushed, a magnitude of the force provided to the second wire by the second driving unit is adjusted on the basis of a friction force generated between the second wire and the second sheath.

4. The power transmission system of claim 3, wherein a magnitude of a maximum force provided to the second wire by the second driving unit is the same as a magnitude of the friction force generated between the second wire and the second sheath.

5. The power transmission system of claim 1, wherein, in a case in which the first driving unit provides a force to the first wire in a direction in which the first wire is pulled and the second driving unit provides a force to the second wire in a direction in which the second wire is pushed, a magnitude of the force provided to the first wire by the first driving unit is the same as a sum of a magnitude of a friction force generated between the first wire and the first sheath and a magnitude of a force which moves the joint of the robot.

6. The power transmission system of claim 1, wherein, in a case in which the first driving unit provides a force to the first wire in a direction in which the first wire is pulled and the second driving unit provides a force to the second wire in a direction in which the second wire is pushed, a partial length, which includes an end portion of the second sheath into which the second wire is inserted, of an entire length of the second sheath is in a state in which movement of the partial length is prevented with the second wire.

7. The power transmission system of claim 1, further comprising:
a body part;
a first elastic part of which one end is fixed to the body part and the other end is fixed to the first driving unit and which wraps the other end of the first wire; and
a second elastic part of which one end is fixed to the body part and the other end is fixed to the second driving unit and which wraps the other end of the second wire,
wherein the first driving unit and the second driving unit move linearly.

8. The power transmission system of claim 7, further comprising a control part disposed in the body part,
wherein the control part controls:
the first driving unit to provide the force to the first wire in the first direction; and
the second driving unit to provide the force to the second wire in the second direction opposite to the first direction.

9. The power transmission system of claim 8, wherein each of the first elastic part and the second elastic part receives a force in the first direction to contract and receives a force in the second direction to extend.

10. The power transmission system of claim 7, wherein a first wire hole through which the first wire passes and a second wire hole through which the second wire passes are formed in one side of the body part.

11. The power transmission system of claim 10, wherein:
the first driving unit includes a first driving motor which generates a driving force and a first moving part which receives the driving force of the first driving motor to move linearly; and
the second driving unit includes a second driving motor which generates a driving force and a second moving part which receives the driving force of the second driving motor to move linearly.

12. The power transmission system of claim 11, wherein the body part includes:
a first guide hole which guides the first moving part; and
a second guide hole which guides the second moving part.

13. A cartridge type power transmission system for driving a robot joint, which is a power transmission system for driving a joint of a robot, the cartridge type power transmission system comprising:
a housing;
a first driving part disposed in the housing and moved linearly; and
a cartridge inserted into the housing,
wherein the cartridge includes a case, a moving part accommodated in the case, connected to the first driving part, and moved linearly, a force transmission part including a sheath formed to have a predetermined length, flexibility, and a hollow shape and a wire which is inserted into the sheath, of which one end is fixed to a joint of a robot and the other end is fixed to the moving part, and which passes through the case, and an elastic part of which one end is fixed to the case and the other end is fixed to the moving part and which wraps the wire, and
the cartridge is detachably coupled to the housing.

14. The cartridge type power transmission system of claim 13, further comprising a second driving part which moves the first driving part so that the first driving part is connected to or separated from the moving part.

15. The cartridge type power transmission system of claim 14, wherein the first driving part includes:
a driving body part which is movable in the housing;
a first motor disposed in the driving body part; and
a detachable part connected to the first motor, moved linearly by a driving force of the first motor, and detachably coupled to the moving part.

16. The cartridge type power transmission system of claim 15, wherein the second driving part includes:
a second motor disposed in the housing; and
a connection part connected to the second motor and moved linearly by a driving force of the second motor.

17. The cartridge type power transmission system of claim 15, wherein:
the detachable part includes a protrusion protruding from an outer surface of the detachable part; and
the moving part includes a detachable groove into which the protrusion of the detachable part is inserted.

18. The cartridge type power transmission system of claim 17, wherein the cartridge includes a hole through which the force transmission part passes.

19. The cartridge type power transmission system of claim 17, wherein the case includes a guide hole which guides movement of the moving part.

20. The cartridge type power transmission system of claim 17, wherein the elastic part extends in a first direction and contracts in a second direction opposite to the first direction.

* * * * *